US011872215B2

(12) United States Patent
Boons

(10) Patent No.: US 11,872,215 B2
(45) Date of Patent: Jan. 16, 2024

(54) SITE-SPECIFIC ANTIBODY-DRUG GLYCONJUGATES AND METHODS

(71) Applicant: UNIVERSITY OF GEORGIA RESEARCH FOUNDATION, INC., Athens, GA (US)

(72) Inventor: Geert-Jan Boons, Athens, GA (US)

(73) Assignee: University of Georgia Research Foundation, Inc., Athens, GA (US)

(*) Notice: Subject to any disclaimer, the term of this patent is extended or adjusted under 35 U.S.C. 154(b) by 71 days.

(21) Appl. No.: 17/155,663

(22) Filed: Jan. 22, 2021

(65) Prior Publication Data

US 2021/0137894 A1 May 13, 2021

Related U.S. Application Data

(62) Division of application No. 15/300,479, filed as application No. PCT/US2015/024969 on Apr. 8, 2015, now Pat. No. 10,905,678.

(60) Provisional application No. 61/976,853, filed on Apr. 8, 2014.

(51) Int. Cl.
C07K 16/00 (2006.01)
A61K 31/4188 (2006.01)
C07K 16/28 (2006.01)
A61K 47/68 (2017.01)
A61K 49/00 (2006.01)

(52) U.S. Cl.
CPC ...... *A61K 31/4188* (2013.01); *A61K 47/6803* (2017.08); *A61K 47/6809* (2017.08); *A61K 47/6849* (2017.08); *A61K 49/0043* (2013.01); *A61K 49/0058* (2013.01); *C07K 16/00* (2013.01); *C07K 16/2803* (2013.01); *C07K 2317/41* (2013.01); *C07K 2317/92* (2013.01)

(58) Field of Classification Search
None
See application file for complete search history.

(56) References Cited

U.S. PATENT DOCUMENTS

| 8,012,322 | B2 | 9/2011 | Park et al. |
| 8,133,515 | B2 | 3/2012 | Boons et al. |
| 8,716,033 | B2 | 5/2014 | Agnew et al. |
| 8,859,629 | B2 | 10/2014 | van Delft et al. |
| 8,940,859 | B2 | 1/2015 | Boons et al. |
| 9,222,940 | B2 | 12/2015 | Van Delft et al. |
| 9,227,943 | B2 | 1/2016 | Boons et al. |
| 9,504,758 | B2 | 11/2016 | Van Delft et al. |
| 9,636,421 | B2 | 5/2017 | Verkade et al. |
| 9,725,405 | B2 | 8/2017 | Boons et al. |
| 2005/0031584 | A1 | 2/2005 | Defrees et al. |
| 2007/0190597 | A1* | 8/2007 | Agnew .......... C07K 14/47 435/68.1 |
| 2009/0068738 | A1 | 3/2009 | Bertozzi et al. |
| 2012/0058111 | A1 | 3/2012 | Ehlers et al. |
| 2012/0197012 | A9 | 8/2012 | Popik et al. |
| 2013/0137763 | A1 | 5/2013 | van Delft et al. |
| 2013/0217863 | A1 | 8/2013 | Vermot-Desroches |
| 2013/0295019 | A1 | 11/2013 | Wu et al. |
| 2013/0310570 | A1 | 11/2013 | Boons et al. |
| 2015/0125892 | A1 | 5/2015 | van Delft et al. |
| 2015/0258210 | A1 | 9/2015 | van Delft et al. |
| 2015/0320882 | A1 | 11/2015 | van Delft et al. |
| 2016/0106860 | A1 | 4/2016 | Satomaa et al. |
| 2016/0107999 | A1 | 4/2016 | van Delft et al. |
| 2016/0214917 | A1 | 7/2016 | van Delft et al. |
| 2016/0235861 | A1 | 8/2016 | van Delft et al. |
| 2016/0250347 | A1 | 9/2016 | van Delft et al. |
| 2016/0257764 | A1 | 9/2016 | van Delft et al. |
| 2016/0280797 | A1 | 9/2016 | van Delft et al. |

FOREIGN PATENT DOCUMENTS

| CN | 101925366 A | 12/2010 |
| CN | 104529711 A | 4/2015 |
| EP | 2 292 273 A2 | 3/2011 |
| EP | 2 222 341 B1 | 2/2015 |
| EP | 2 907 525 A2 | 8/2015 |
| JP | 5498952 B2 | 3/2014 |
| JP | 5956487 B2 | 6/2016 |
| JP | 2016-145221 A | 8/2016 |
| WO | WO 2009/064366 A2 | 5/2009 |

(Continued)

OTHER PUBLICATIONS

Boons, Geert-Jan, "A Fully Synthetic Carbohydrate-Based Cancer Vaccine," Grant Abstract, Grant No. R01CA088986 [online]. National Institutes of Health, project dates May 1, 2011 to Mar. 31, 2018 [retrieved on Oct. 4, 2017]. Retrieved from the Internet: <URL:https://projectreporter.nih.gov/pr_Prj_info_desc_dtls.cfm?aid=8826031&icde=36329420&ddparam=&ddvalue=&ddsub=&cr=1&csb=default&cs=ASC&pball=&print=yes>; 3 pgs.

Azadi, Parastoo, "Training" Grant Abstract, Grant No. P41GM103390 [online]. National Institutes of Health, budget start date Feb. 1, 2017 to Jan. 31, 2018 [retrieved on Oct. 4, 2017]. Retrieved from the Internet: <URL:https://projectreporter.nih.gov/pr_Prj_info_desc_dtls.cfm?aid=9222766&icde=36329636&ddparam=&ddvalue=&ddsub=&cr=3&csb=default&cs=ASC&pball=&print=yes>; 2 pages.

International Patent Application No. PCT/US2015/024969, filed Apr. 8, 2015; International Search Report and Written Opinion dated Jul. 13, 2015; 11 pages.

International Patent Application No. PCT/US2015/024969, filed Apr. 8, 2015; International Preliminary Report on Patentability dated Oct. 20, 2016; 9 pages.

(Continued)

*Primary Examiner* — Benjamin P Blumel
(74) *Attorney, Agent, or Firm* — Meunier Carlin & Curfman LLC

(57) ABSTRACT

Compounds, compositions, and methods are provided for covalently linking an antibody or an antibody fragment to a cargo molecule, such as a therapeutic or a diagnostic agent, using a combination of enzymatic glycan remodeling and click chemistry. The method allows a cargo molecule to be selectively and efficiently attached post-translationally to an antibody or an antibody fragment. Also provided are antibody drug conjugates, methods of making, and uses thereof.

22 Claims, 17 Drawing Sheets

(56) References Cited

FOREIGN PATENT DOCUMENTS

| | | |
|---|---|---|
| WO | WO 2009/067663 A1 | 5/2009 |
| WO | WO 2011/136645 A1 | 3/2011 |
| WO | WO 2012/047663 A2 | 4/2012 |
| WO | WO 2014/043361 A1 | 3/2014 |
| WO | WO 2014/065661 A1 | 5/2014 |
| WO | WO 2014/177771 A1 | 11/2014 |
| WO | WO 2015/057063 A1 | 4/2015 |
| WO | WO 2015/057064 A1 | 4/2015 |
| WO | WO 2015/057065 A1 | 4/2015 |
| WO | WO 2015/157446 A1 | 10/2015 |

OTHER PUBLICATIONS

Adair et al., "Antibody-drug conjugates—a perfect synergy" Expert Opin. Biol. Ther. Sep. 2012; 12(9):1191-206. Epub Jun. 1, 2012.

Alves et al., "Selective photocrosslinking of functional ligands to antibodies via the conserved nucleotide binding site" Biomaterials, Jul. 2013, 34(22):5700-10. Epub Apr. 16, 2013.

Alves et al., "Conjugation of a reactive thiol at the nucleotide binding site for site-specific antibody functionalization" Bioconjug. Chem., Jul. 16, 2014; 25(7):1198-202. Epub Jun. 23, 2014.

Angelino et al., "Versatile intermediates in the selective modification of the amino function of 2-amino-2-deoxy-D-mannopyranose and the 3-position of 2-acetamido-2-deoxy-D-mannose: potential membrane modifiers in neoplastic control" Carbohydr. Res., Oct. 16, 1995; 276(1):99-115.

Anumula et al., "A comprehensive procedure for preparation of partially methylated alditol acetates from glycoprotein carbohydrates" Anal Biochem, May 15, 1992; 203(1):101-8.

Appelhans et al., "Dendritic glycopolymers based on dendritic polyamine scaffolds: view on their synthetic approaches, characteristics and potential for biomedical applications" Chem Soc Rev, Jun. 21, 2015; 44(12):3968-96. Epub Dec. 18, 2014.

Axup et al., "Synthesis of site-specific antibody-drug conjugates using unnatural amino acids" Proc. Natl. Acad. Sci. U. S. A., Oct. 2, 2012; 109(40):16101-6.

Barb et al., "NMR characterization of immunoglobulin G Fc glycan motion on enzymatic sialylation" Biochemistry, Jun. 5, 2012; 51(22):4618-26. Epub May 22, 2012.

Biogeneration Ventures, "SynAffix raises Series A investment round to advance its GlycoConnect™ technology for creating next-generation ADCs" Feb. 18, 2014; [retrieved on Oct. 4, 2017]. Retrieved from the Internet: <URL:http://www.biogenerationventures.com/userdata/file/SynAffix%20financing%2018%20February%202014%20-%20Final.pdf> 2 pages.

Boeggeman et al., "Site specific conjugation of fluoroprobes to the remodeled Fc N-glycans of monoclonal antibodies using mutant glycosyltransferases: application for cell surface antigen detection" Bioconjug Chem, Jun. 2009; 20(6):1228-36.

Coligan et al., Current Protocols in Immunology, Greene Pub. Assoc. & Wiley Interscience: New York, NY; 1991; Core publication: Cover page, title page and table of contents. 14 pages.

Debets et al. "Aza-dibenzocyclooctynes for fast and efficient enzyme PEGylation via copper-free (3+2) cycloaddition" ChemComm, 2010; 46:97-99.

Debets et al., "Azide: A Unique Dipole for Metal-Free Bioorthogonal Ligations" ChemBioChem, 2010; 11:1168-84.

Debets et al. "Bioconjugation with Strained Alkenes and Alkynes". 2011. Acc. Chem. Res. 44:805-815.

Dennler et al., "Transglutaminase-Based Chemo-Enzymatic Conjugation Approach Yields Homogeneous Antibody-Drug Conjugates" Bioconjugate Chem, Mar. 19, 2014; 25(3):569-78. Epub Feb. 12, 2014.

Dennler et al., "Antibody Conjugates: From Heterogeneous Populations to Defined Reagents" Antibodies, Aug. 3, 2015; 4:197-224. Epub Aug. 3, 2015.

Dicken et al., "Reactions at High Pressures. [3 + 2] Dipolar Cycloaddition of Nitrones with Vinyl Ethers" J. Org. Chem. 1982; 47:2047-51.

Ducry et al., "Antibody-drug conjugates: linking cytotoxic payloads to monoclonal antibodies" Bioconjug. Chem., Jan. 2010; 21(1):5-13.

Eschenfelder and Brossmer, "A new approach to the synthesis of 5-N-acetyl-D-neuraminic acid α-ketosides" Carbohydr. Res. Jan. 1, 1980, 78(1):190-194.

Goodfellow et al., "An Endoglycosidase with Alternative Glycan Specificity Allows Broadened Glycoprotein Remodelling" J Am Chem Soc, May 16, 2012; 134(19):8030-3. Epub May 2, 2012.

Harlow et al., Antibodies: A Laboratory Manual, Cold Spring Harbor Laboratory Press, Cold Spring Harbor, NY; copyright 1988. Title page, publisher's page, and table of contents only (8 pages).

Huang et al., "Chemoenzymatic glycoengineering of intact IgG antibodies for gain of functions" J. Am. Chem. Soc., Jul. 25, 2012; 134(29):12308-18. Epub Jul. 16, 2012.

Hutchins et al., "Site-specific coupling and sterically controlled formation of multimeric antibody fab fragments with unnatural amino acids" J. Mol. Biol., Mar. 4, 2011; 406(4):595-603. Epub Jan. 13, 2011.

Iyer et al., "Antibody drug conjugates—Trojan horses in the war on cancer" J. Pharmacol. Toxicol. Methods, Nov.-Dec. 2011; 64(3):207-212. Epub Aug. 6, 2011.

Jacobs et al., "Substrate specificity of the sialic acid biosynthetic pathway" Biochemistry, Oct. 30, 2001; 40(43):12864-74.

Jefferis, "Glycosylation as a strategy to improve antibody-based therapeutics" Nat. Rev. Drug Discov., Mar. 2009; 8(3):226-34.

Jewett et al. "Cu-free click cycloaddition reactions in chemical biology". 2010. Chem. Soc. Rev. 39(4):1272-1279.

Junutula et al., "Site-specific conjugation of a cytotoxic drug to an antibody improves the therapeutic index" Nat. Biotechnol., Aug. 2008; 26(8):925-32. Epub Jul. 20, 2008.

Kabat et al., Sequences of Proteins of Immunological Interest, U.S. Dept. of Health and Human Services, Public Health Service, National Institutes of Health: Bethesda, MD; 1991. vol. 1, 5th Ed., NIH Publication No. 91-3242. Cover page, title page and table of contents. 7 pages.

Kajihara et al., "Synthesis of CMP-9"—modified-sialic acids as donor substrate analogues for mammalian and bacterial sialyltransferases Carbohydr. Res., Sep. 3, 2007; 342(12-13):1680-8. Epub Jun. 5, 2007.

Kennedy et al., "Cellular consequences of copper complexes used to catalyze bioorthogonal click reactions" J. Am. Chem. Soc., Nov. 9, 2011; 133(44):17993-8001. Epub Oct. 19, 2011.

Keppler et al., "Biochemical engineering of the N-acyl side chain of sialic acid: biological implications" Glycobiology, Feb. 2001; 11(2):11R-18R.

Kitson et al., "Antibody-Drug Conjugates: Carbon-14 Labeling Requirements" Published in Drug Discovery & Development, May 30, 2013; [retrieved on Oct. 4, 2017]. Retrieved from the Internet: <URL:https://www.dddmag.com/article/2013/05/antibody-drug-conjugates-carbon-14-labeling-requirements> 9 pages.

Kohler and Milstein, "Continuous cultures of fused cells secreting antibody of predefined specificity" Nature, Aug. 7, 1975; 256(5517):495-7.

Li et al., "The Preparation of Well-Defined Antibody-Drug Conjugates through Glycan Remodeling and Strain-Promoted Azide-Alkyne Cycloadditions" Angew. Chem. Int. Ed. Engl., Jul. 7, 2014; 53:7179-82. Epub May 23, 2014.

Mbua et al., "Selective exo-enzymatic labeling of N-glycans on the surface of living cells by recombinant ST6Gal I" Angewandte Chem Int Ed Engl, Dec. 2, 2013; 52(49):13012-5. Epub Oct. 15, 2013.

Meldal et al. "Cu-catalyzed azide-alkyne cycloaddition" Chem. Rev. Aug. 2008; 108(8):2952-3015.

Molina, "A decade of rituximab: improving survival outcomes in non-Hodgkin's lymphoma" Annu Rev Med, 2008; 59:237-50.

Morell et al., "Physical and chemical studies on ceruloplasmin. IV. Preparation of radioactive, sialic acid-free ceruloplasmin labeled with tritium on terminal D-galactose residues" J. Biol. Chem., Aug. 25, 1966; 241(16):3745-9.

(56) References Cited

OTHER PUBLICATIONS

Ning et al., "Visualizing Metabolically Labeled Glycoconjugates of Living Cells by Copper-Free and Fast Huisgen Cycloadditions" Angew. Chem. Int. Ed. Engl., Mar. 7, 2008; 47(12):2253-2255.
Ning et al., "Protein Modification by Strain-Promoted Alkyne-Nitrone Cycloaddition" Angew. Chem. Int. Ed, 2010; 49:3065-68.
Ning et al., "Protein Modification by Strain-Promoted Alkyne-Nitrone Cycloaddition" Supporting Information, Angew. Chem. Int. Ed, 2010; 22 pages.
Okeley et al., "Metabolic engineering of monoclonal antibody carbohydrates for antibody-drug conjugation" Bioconjug. Chem., Oct. 16, 2013; 24(10):1650-5. Epub Sep. 19, 2013.
O'Shannessy et al., "A novel procedure for labeling immunoglobulins by conjugation to oligosaccharide moieties" Immunology Letters, Jan. 1, 1984; 8(5):273-7.
Panowski et al., "Site-specific antibody drug conjugates for cancer therapy" MAbs, Jan.-Feb. 2014; 6(1):34-45. Epub Nov. 1, 2013.
Parhi and Franck, "A Weinreb nitrile oxide and nitrone for cycloaddition" Org. Lett., Sep. 2, 2004; 6(18):3063-5.
Patterson et al., "Functionalized Cyclopropenes as Biorthogonal Chemical Reporters" J Amer Chem Soc, Oct. 16, 2012; 134:18638-43.
Rodwell et al., "Site-specific covalent modification of monoclonal antibodies: in vitro and in vivo evaluations" Proc. Natl. Acad. Sci. U. S. A., Apr. 1986; 83(8):2632-6.
Saarinen, "Glycolinkers for Antibody-Drug Conjugates" World ADC San Francisco, Conference Presentation, San Francisco, California, Oct. 16, 2013, 32 pgs.
Sanders et al., "Metal Free Sequential [3+2]-Dipolar Cycloadditions using Cyclooctynes and 1,3-Dipoles of Different Reactivity" J Amer Chem Soc, Feb. 2, 2011; 133(4):949-57.
Saxon and Bertozzi, "Cell surface engineering by a modified Staudinger reaction" Science, Mar. 17, 2000; 287(5460):2007-10.
Schilling et al., "Bioconjugation via azide-Staudinger ligation: an overview" Chem. Soc. Rev., Sep. 2011; 40(9):4840-71. Epub Jun. 17, 2011.
Schmaltz et al., "Enzymes in the synthesis of glycoconjugates" Chem. Rev., Jul. 13, 2011; 111(7):4259-307.
Selvaraj et al., "trans-Cyclooctene—a stable, voracious dienophile for bioorthogonal labeling" Curr. Opin. Chem Biol., Oct. 2013; 17(5):753-60. Epub Aug. 23, 2013.
Shade et al., "Antibody Glycosylation and Inflammation" Antibodies, 2013; 2:392-414. Epub Jun. 25, 2013.
Song et al., "Tin-free radical alkylation of ketones via N-silyloxy enamines" Chem. Commun. (Camb), Jul. 21, 2006; (27):2893-5.
Soriano Del Amo et al., "Biocompatible copper(I) catalysts for in vivo imaging of glycans" J Am Chem. Soc., Dec. 1, 2010; 132(47):16893-9. Epub Nov. 9, 2010.
Strop et al., "Location Matters: Site of Conjugation Modulates Stability and Pharmacokinetics of Antibody Drug Conjugates" Chem. Biol., Feb. 21, 2013; 20(2):161-7.

"Key Features of Synaffix ADC" Web page [online]. Synaffix, [retrieved on or before Mar. 25, 2014]. Retrieved from the Internet: <URL: http://www.synaffix.com/technology/>. <URL: http://www.synaffix.com/adc/>; 3 pages.
Thorsten, "Selective Staining of Infection-Mobilized Leukocytes by Common Food Dyes Using Chromium Trioxide as a Fixative / Mordant" Jun. 2007; [retrieved on Oct. 4, 2017]. Retrieved from the CR Scientific LLC Website on the Internet: <URL:http://www.crscientific.com/article-5-min-stain-CrO3.html> 9 pages.
Tian et al., "1,3-Dipolar Cycloaddition Reactions of Nitrones to Prop-1-ene-1,3-sultone" Synthesis, Jul. 2003; 2003(9):1329-34.
Van Boeckel et al., "Synthesis of a Pentasaccharide Corresponding to the Antithrombin III Binding Fragment of Heparin" J Carbohydr Chem, 1985; 4(3):293-321.
Van Lenten et al., "Studies on the chemical and enzymatic modification of glycoproteins. A general method for the tritiation of sialic acid-containing glycoproteins" J. Biol. Chem., Mar. 25, 1971; 246(6):1889-94.
Varki, "Glycan-based interactions involving vertebrate sialic-acid-recognizing proteins" Nature, Apr. 26, 2007; 446(7139):1023-9.
Wu and Wu, "Receptor-mediated in Vitro Gene Transformation by a Soluble DNA Carrier System" J Biol Chem, Apr. 5, 1987; 262(10):4429-32.
Yamamoto, "Modification and application of glycosidases to create homogeneous glycoconjugates" Abstract for Doctoral Thesis, University of Oxford, 2013 [retrieved on Oct. 20, 2017]. Retrieved from the Internet: <URL: https://oatd.org/oatd/record?record=oai%5C%3Aethos.bl.uk%5C%3A581357>3 pages.
Yang et al., "Live-Cell Imaging of Cyclopropene Tags with Fluorogenic Tetrazine Cycloadditons" Angew. Chem. Int. Ed., 2012; 51:7476-9.
Yu et al., "A multifunctional Pasteurella multocida sialyltransferase: a powerful tool for the synthesis of sialoside libraries" J. Am. Chem. Soc., Dec. 21, 2005; 127(50):17618-9.
Zolot et al., "Antibody-drug conjugates" Nat. Rev. Drug Discov., Apr. 2013; 12(4):259-60.
Zou et al., "Trityl-derivatized carbohydrates immobilized on a polystyrene microplate" Carbohydr. Res., Nov. 24, 2008; 343(17):2932-8. Epub Aug. 28, 2008.
Zuberbuhler et al., "Fucose-specific conjugation of hydrazide derivatives to a vascular-targeting monoclonal antibody in IgG format" Chem. Commun. (Camb), Jul. 18, 2012; 48(56):7100-2. Epub Jun. 11, 2012.
Gross et al., "Transfer of synthetic sialic acid analogues to N- and O-linked glycoprotein glycans using four different mammalian sialyltransferases" Biochemistry, Jan. 1, 1989; 28:7386-92.
Zhou et al., "Site Specific Antibody-Drug Conjugation through Glycoengineering" Bioconjugate Chemistry, Mar. 19, 2014; 25(3):510-20; epub Feb. 17, 2014.
Rochefort et al. "Metabolic exploitation of the sialic acid biosynthetic pathway to generate site-specifically labeled antibodies," Glycobiology vol. 24, No. 1, pp. 62-69 (2014).

* cited by examiner

A

C

C-5 azide-containing derivative

C-5 nitrone-containing derivative

C-5 diazo-containing derivative

D

SITE-SPECIFIC ANTIBODY-DRUG GLYCONJUGATES AND METHODS

This application is a divisional of U.S. application Ser. No. 15/300,479, filed Sep. 29, 2016, as a § 371 Application of PCT/2015/024969, filed Apr. 8, 2015, which claims the benefit of U.S. Provisional Application Ser. No. 61/976,853, filed Apr. 8, 2014, each of which is incorporated herein by reference in its entirety.

STATEMENT OF GOVERNMENT RIGHTS

This invention was made with government support under Grant Nos. R01CA088986, P41RR005351, and P41GM103390, awarded by the National Institutes of Health. The government has certain rights in the invention.

BACKGROUND

Antibody-drug conjugates (ADC) have considerable promise as anticancer agents by selectively targeting cytotoxic drugs to cells expressing tumor-associated cell surface proteins (Iyer et al., J. Pharmacol. Toxicol. Methods 2011, 64:207-212; Adair et al., Expert Opin. Biol. Ther. 2012, 12:1191-1206). It has been proposed that ADCs are endocytosed after binding a cell-surface protein and degraded in the lysosome to release the cytotoxic drug. Alternatively, a drug can be attached to an antibody through a linker that is selectively cleaved after cellular uptake (Ducry et al., Bioconjug. Chem. 2010, 21:5-13). The promise of the ADC technology has been demonstrated by the approval of a CD30 (brentuximab) and a Her2 (ERBB2) specific ADC for treatment of Hodgkin's lymphoma and metastatic breast cancer, respectively (Zolot et al., Nat. Rev. Drug Discov. 2013, 12:259-260).

In typical antibody-drug conjugates (ADCs), cytotoxic drugs are nonselectively linked to antibodies by electrophilic modification of lysine or cysteine residues using N-hydroxysuccinimide ester or maleimide-activated drugs, respectively (Ducry et al., Bioconjug. Chem. 2010, 21: 5-13). These conjugation methods yield heterogeneous mixtures of products that differ in the sites and stoichiometry of modification.

ADCs have been produced from antibodies that incorporate additional cysteines (Junutula, et al., Nat. Biotechnol. 2008, 26:925-932) unnatural amino acids (Hutchins et al., J. Mol. Biol. 2011, 406:595-603; Axup et al., Proc. Natl. Acad. Sci. U.S.A. 2012, 109:16101-16106) or tags for transamination reactions (Strop et al., Chem. Biol. 2013, 20:161-167). These approaches have yielded ADCs with less heterogeneity and hence improved therapeutic and pharmacokinetic properties in animal models; however, their production is cumbersome and their utility limited in that they typically require genetic engineering of the antibody of interest.

SUMMARY OF THE INVENTION

Control over the site(s) and stoichiometry of conjugation is important for the development of next-generation antibody-drug conjugates (ADCs) because these parameters have a significant impact on the conjugates' pharmacokinetic properties. Moreover, a conjugation method that can be applied post-translationally would allow any antibody of interest, whether naturally occurring or genetically engineered, to serve as a platform for antibody-drug conjugation. The present invention advances the art by providing functionalized antibodies, as well as site-specific antibody conjugates, such as antibody-drug conjugates, having conjugation sites at well-defined glycosylated amino acid residues. Moreover, conjugation is carried out post-translationally, thereby making possible any antibody/drug pairing of interest, without the need to resort to additional genetic engineering or mutagenesis.

In one aspect, the invention provides an antibody which includes a functionalized N-linked oligosaccharide. Also included in the invention is an antibody fragment, preferably a heavy chain antibody fragment, which includes a functionalized N-linked oligosaccharide. It should be understood that references herein to functionalized antibodies are intended to be inclusive of antibody fragments thereof that contain the functionalized N-linked oligosaccharide. Moreover, the invention includes molecules that include, or are covalently linked to, the functionalized antibody of the invention or functionalized fragment thereof. Additionally, while the invention is described herein primarily with respect to N-linked oligosaccharides, such as asparagine-linked or glutamine-linked oligosaccharides, the invention involves glycan remodeling procedures that can readily be applied to O-linked oligosaccharides as well, including oligosaccharides attached to a glycoprotein at a serine, threonine or tyrosine. Such applications, including compounds, compositions and methods involving O-linked oligosaccharides, are encompassed by the invention as well.

The functionalized antibody can be a polyclonal or monoclonal antibody. Preferably, the functionalized antibody is a human or humanized monoclonal antibody. A preferred functionalized antibody or fragment thereof includes a functionalized IgG antibody or fragment thereof. A functionalized antibody fragment preferably includes all or a portion of an Fc fragment or Fc-hinge fragment, which preferably includes a CH2 region, a CH3 region, or both. In a particularly preferred embodiment, the functionalized antibody or fragment thereof includes a functionalized N-linked oligosaccharide at position Asn297 of the immunoglobulin heavy chain, numbered according to the Kabat system. Asn297 is located in the CH2 region of the immunoglobulin heavy chain (see FIG. 1A).

The functionalized antibody or fragment includes a functionalized N-linked oligosaccharide, which can for example be a monoantennary, biantennary, terantennary or tetraantennary glycan. The functionalized N-linked oligosaccharide includes at least one terminal sialic acid moiety, also referred to herein as a functionalized terminal sialic acid. The N-linked oligosaccharide can contain 1, 2, 3, 4, or more functionalized terminal sialic acids. In one embodiment, the N-linked oligosaccharide is a biantennary glycan that includes the at least one functionalized terminal sialic acid. In one embodiment, the functionalized sialic acid includes a functional group selected from the group consisting of an azide, a nitrone, a nitrile oxide, an azoxy, a diazo, an acyl diazo, and a trans-cyclooctene. The functional group can, but need not, be positioned at position C-9 of the sialic acid; the functional group can, but need not, be positioned at C-5 of the sialic acid moiety, or at both the C-9 and C-5 positions, and/or at one or more other positions on the sialic acid.

In another aspect, the invention provides an antibody conjugate, also referred to herein as simply a "conjugate". The antibody conjugate of the invention includes the functionalized antibody or fragment thereof, such as an Fc fragment, as described herein, and a cargo moiety. The cargo moiety or molecule, sometimes referred to as a "payload", is covalently linked to the sialic acid, preferably via the sialic acid functional group, more preferably through reaction with an azide, a nitrone, a nitrile oxide, an azoxy, a diazo, an acyl diazo, and a trans-cyclooctene of the functionalized sialic acid, and preferably at position C-9 or C-5 on the sialic acid. Exemplary cargo molecules can include, without limitation, a cytotoxic drug, a cytostatic agent, a toxin, a radioisotope or radionuclide, a nucleotide, an RNA, a DNA, an antibiotic, an immunosuppressive agent, a fluorophore, a dye, a protein, or any combination thereof. The conjugate can include 1, 2, 3, 4 or more cargo moieties. Optionally, the conjugate can include a linker region positioned between the antibody or fragment thereof, and the cargo constituent. The linker region can be acid-labile, redox active (e.g., a disulfide), and/or proteolytically cleavable.

In yet another aspect, the invention provides a method of making the functionalized antibody or fragment thereof, such as an Fc fragment. The method includes remodeling at least one N-linked oligosaccharide of the antibody or fragment thereof to include a functionalized terminal sialic acid, such as an azido-modified sialic acid. In one embodiment, sialylation of the antibody or fragment thereof is achieved by contacting the antibody or fragment thereof with a functionalized CMP-sialic acid and a sialyltransferase and under conditions and for a time sufficient to attach at least one functionalized sialic acid to an N-linked oligosaccharide of the antibody or fragment thereof, such as an Fc fragment. An exemplary sialyltransferase is ST6Gal 1.

Optionally, the method further includes, prior to the sialylation step, contacting the antibody or Fc fragment thereof with a galactosyltransferase and a UDP-galactose under conditions and for a time sufficient to attach at least one galactose to an N-linked oligosaccharide of the antibody or Fc fragment thereof to yield at least one acceptor site for the sialyl transferase. If the antibody or Fc fragment thereof includes at least two biantennary N-linked oligosaccharides, the method can further include attaching galactose to one or both arms of the biantennary N-linked oligosaccharides to yield a plurality of acceptor sites for the sialyl transferase.

In a preferred embodiment, the method for making a functionalized antibody or fragment thereof, such as an Fc fragment, involves first galactosylating at least one N-linked oligosaccharide of the antibody or fragment thereof to yield at least one galactose acceptor site. For example, the antibody or fragment thereof can be contacted with a β-1,4-galactosyltransferase and a UDP-galactose for a time and under conditions sufficient to covalently attach a galactose to at least one N-linked oligosaccharide. Next, the method involves covalently linking a functionalized sialic acid to the antibody or fragment thereof at the galactose acceptor site. For example, the antibody or fragment thereof can be contacted with an α-2,6-sialyl transferase and a functionalized CMP-sialic acid for a time and under conditions to covalently attach a functionalized sialic acid to the galactose acceptor site. Optionally, the method is extended to attach the cargo molecule, either in an immediately subsequent reaction or at a later point in time, for example after storage of the functionalized antibody or fragment. The method of making the functionalized antibody or fragment thereof thus optionally further includes covalently linking a cargo molecule to the functionalized antibody or fragment thereof at the functionalized sialic acid to yield the conjugate. The invention also provides a method of making an antibody conjugate that utilizes, as a starting material, the functionalized antibody or fragment thereof, such as an Fc fragment, of the invention. The conjugate is made by contacting the functionalized antibody or fragment thereof with a functionalized cargo molecule under conditions and for a time sufficient to form a conjugate.

In preferred methods, the antibody or fragment thereof, and the cargo molecule, are functionalized with functional groups that are selected such that they can participate in a click chemistry reaction to covalently link the two constituents to form the conjugate. In an exemplary embodiment, the functionalized antibody or fragment includes an azido functional group, and the functionalized cargo molecule takes the form of a DIBO-derivative that includes an alkyne functional group. The azido functional group and the alkyne function group can be covalently linked in a chemical click reaction to yield the conjugate. In a one embodiment, the method utilizes metal-free strain-promoted alkyne-azide cycloaddition (SPAAC) chemistry to yield the conjugate.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
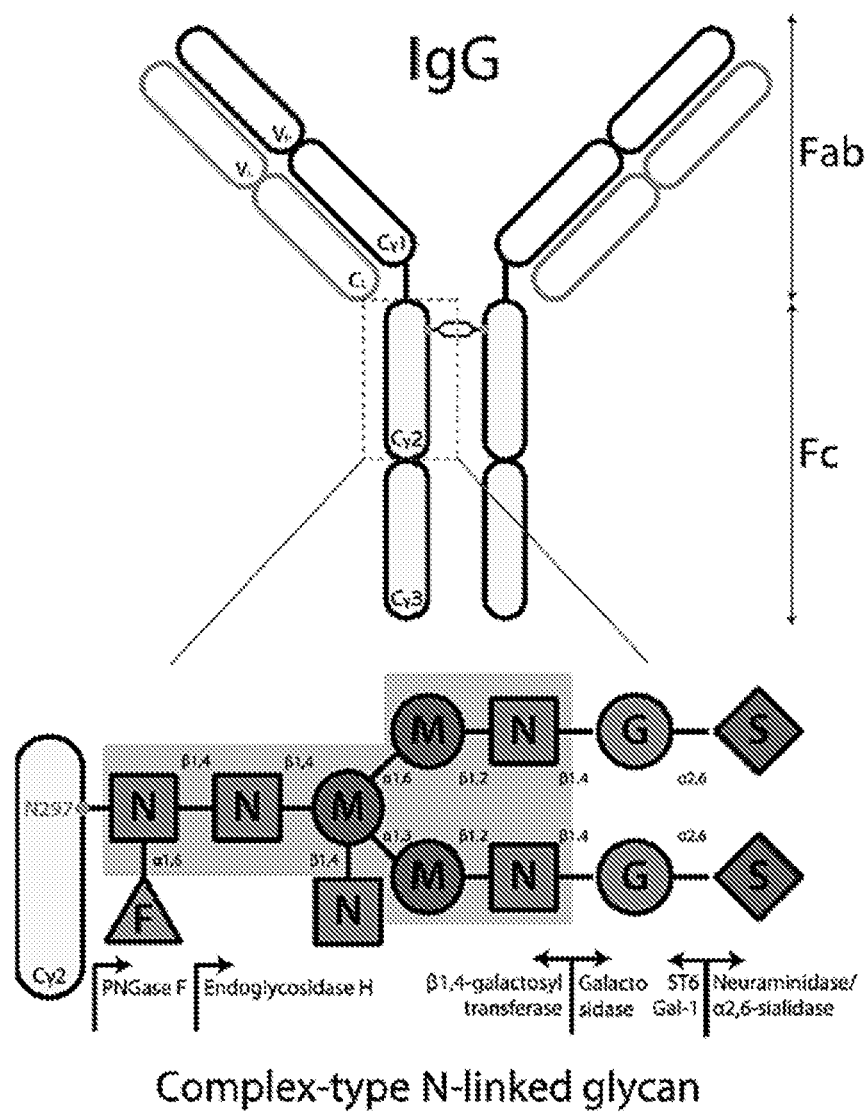
FIG. 1 shows (A) a schematic representation of human IgG structure and glycan composition; each IgG heavy chain has a variable region ($V_H$) and a constant region; the constant region includes containing three domains (Cγ1-3, also known as $C_H1$, $C_H2$, and $C_H3$); the line between Cγ1 (CH1) and Cγ2 (CH2) is termed the hinge region; each light chain also has variable ($V_L$) and constant regions ($C_L$); an IgG molecule contains an antigen-binding fragment (Fab) and fragment crystallizable region (Fc); human IgG is N-glycosylated at position N297 in the $C_H2$ region; the complex N-linked glycan at position 297 typically includes a biantennary heptasaccharide core (gray block) and variable extensions; abbreviations: F, fucose; N, GlcNAc; M, mannose; G, galactose; S, sialic acid; glycosyltransferases (left arrow) and glycosidases (right arrow), responsible for the addition or removal of the specific sugar, respectively, are shown directly underneath of the sugar linkage (adapted from Kai-Ting et al., Antibodies 2013, 2:392-414); (B) glycan remodeling of IgG antibodies to produce a homogeneous N-glycan with azido moieties for strain-promoted cycloadditions with compounds 2-4 (i) UDP-Galactose, UDP-galactosyltransferase, Tris-HCl, BSA/A.P.; (ii) CMP-sialic acid derivative 1 functionalized at position C-9, sialyltransferase, cacodylate buffer pH 7.6, BSA/A. P.; (iii) compounds 2 or 3 or 4; UDP, uridine diphosphate; GlcNAc, N-acetylglucosamine; Man, mannose; Gal, galactose; Fuc, fucose; Sia, sialic acid; CMP, cytidine monophosphate; (C) exemplary functionalized sialic acids showing functionalization at position C-5 with azido, nitrone, and diazo functional groups; (D) exemplary synthesis of a CMP-sialic acid derivative 20 functionalized with azido at position C-5; (E) exemplary synthesis of a CMP-sialic acid derivative 21 with dibenzylcyclooctynol at position C-5, followed by enzymatic reaction with N-acetyllactosamine (LacNAc) to yield a dibenzylcyclooctynol-functionalized trisaccharide 22; compound 21 is also shown linked to a resin via strain-promoted alkyne-azide cycloaddition (SPAAC) with azido-functionalized resin; (F) exemplary synthesis of a CMP-sialic acid derivative 23 with trans-cyclooctene at position C-5, followed by enzymatic reaction with N-acetyllactosamine (LacNAc) to yield a trans-cyclooctene-functionalized trisaccharide 24; compound 23 is also shown in a reaction with a diazo compound in an inverse electron demand Diels-Alder reaction (DARinv).
Figure 1:
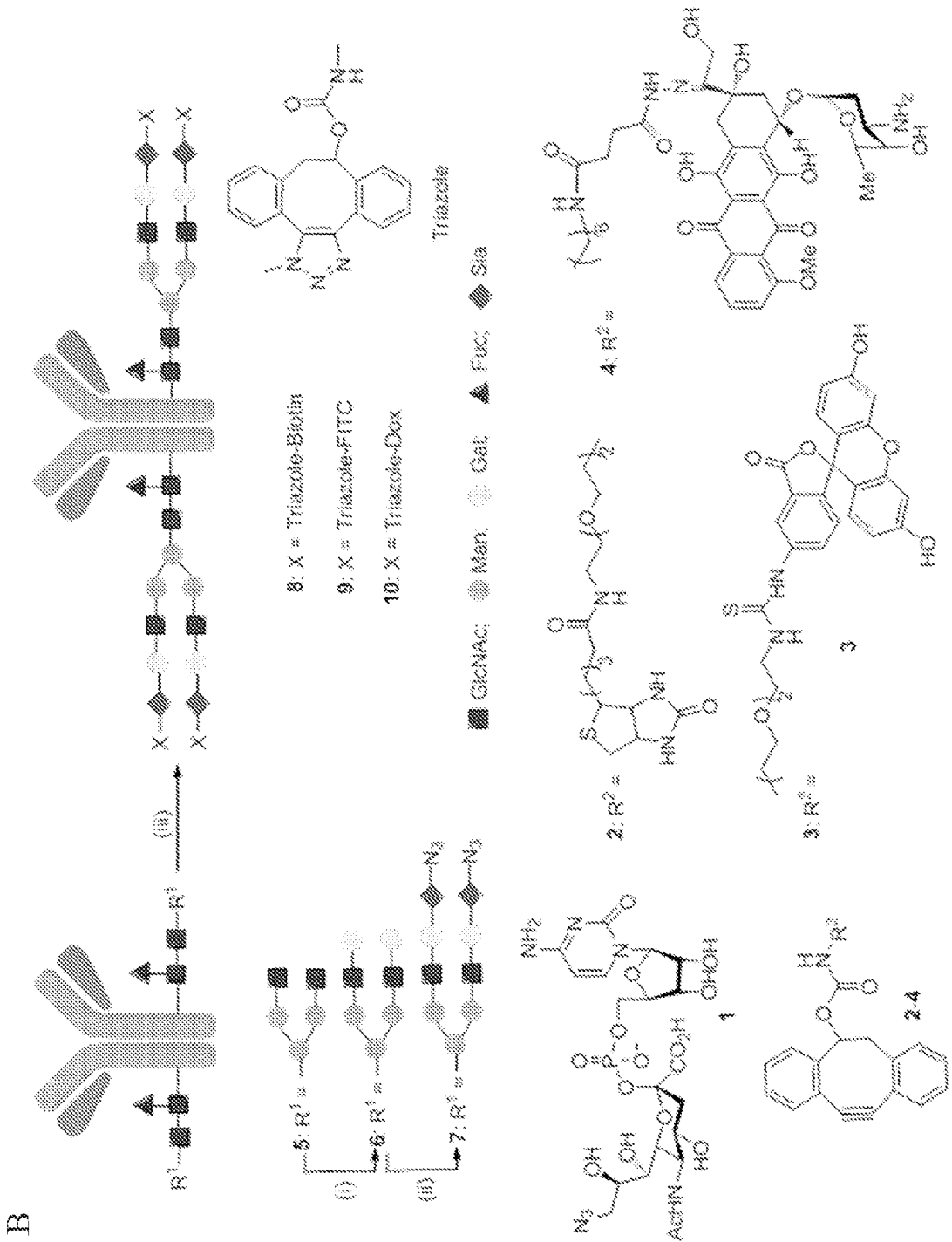
Figure 1:
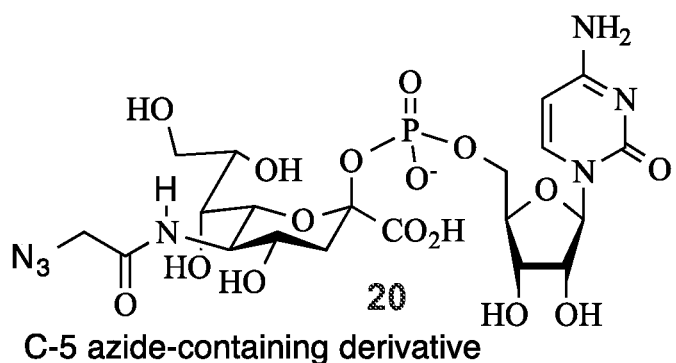
Figure 1:
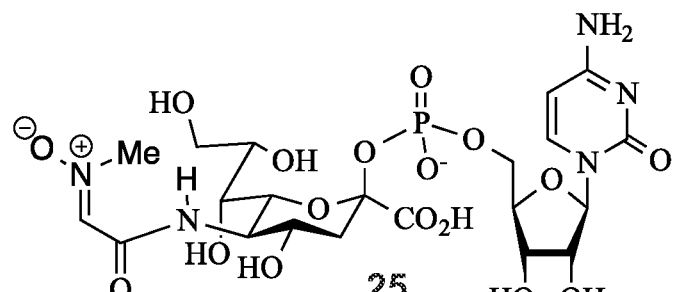
Figure 1:
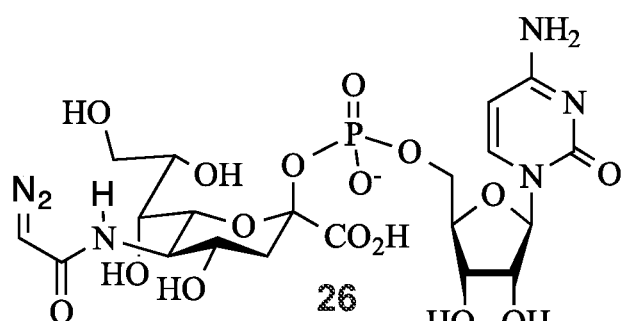
Figure 1:
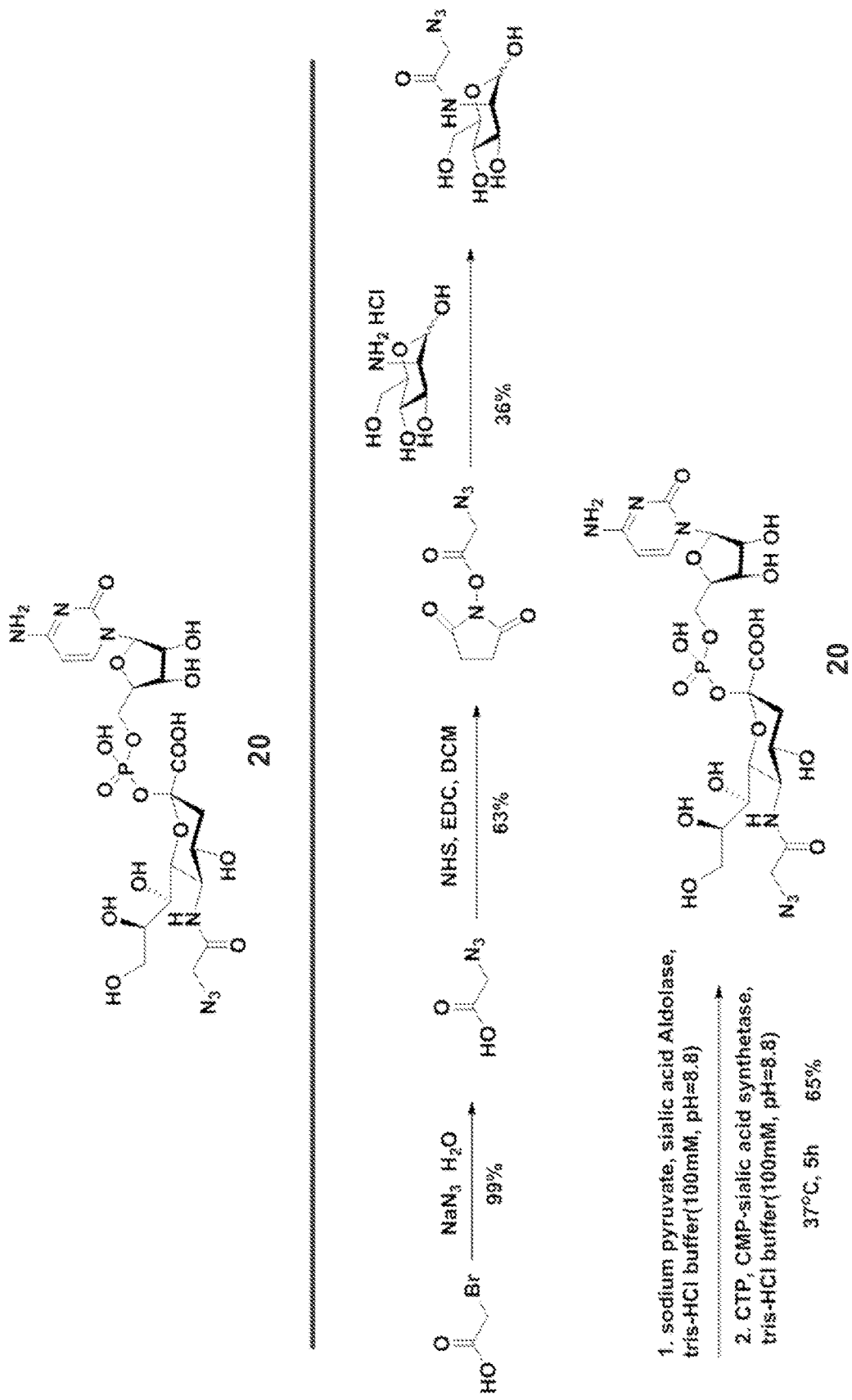
Figure 1:
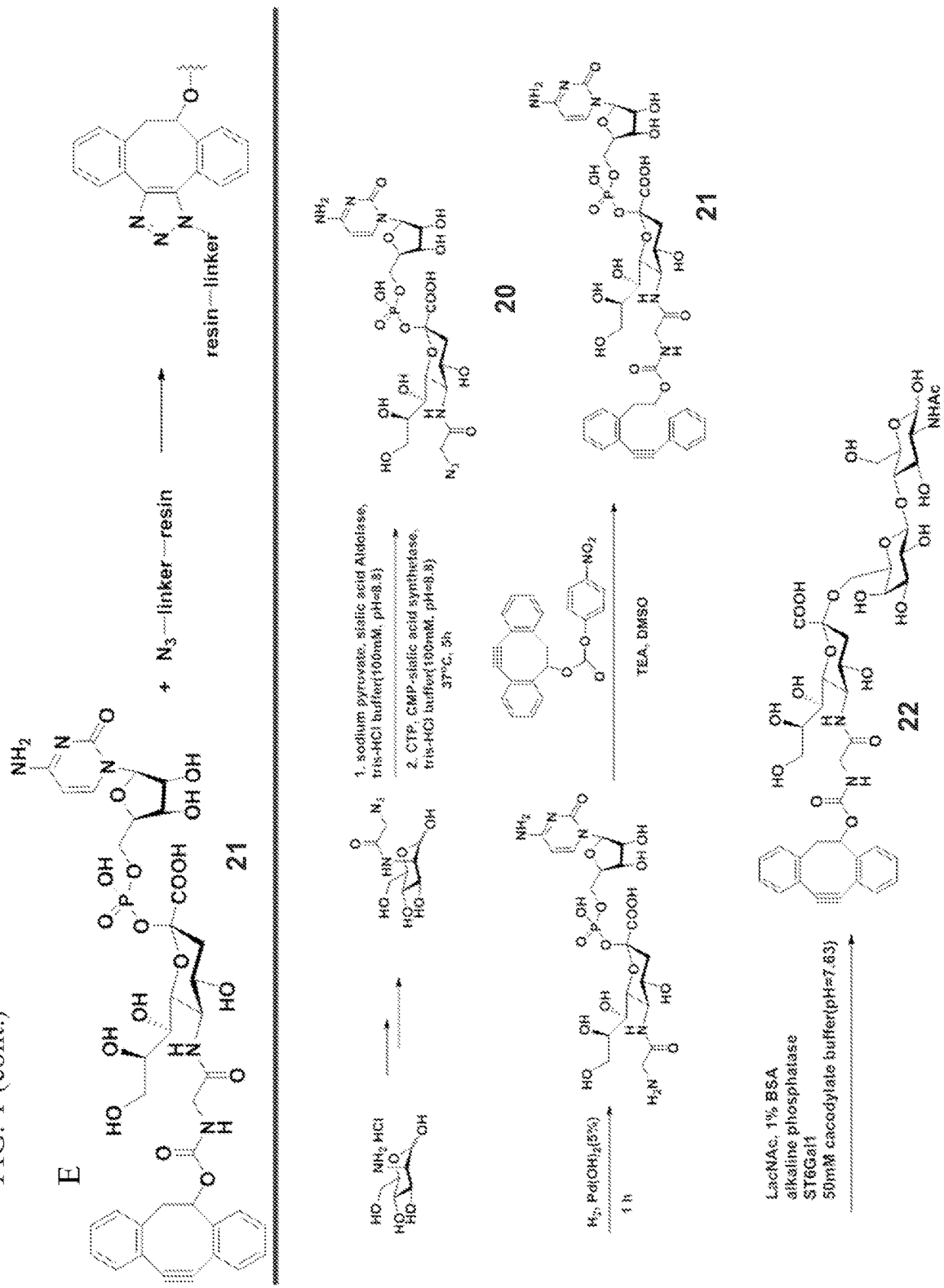
Figure 1:
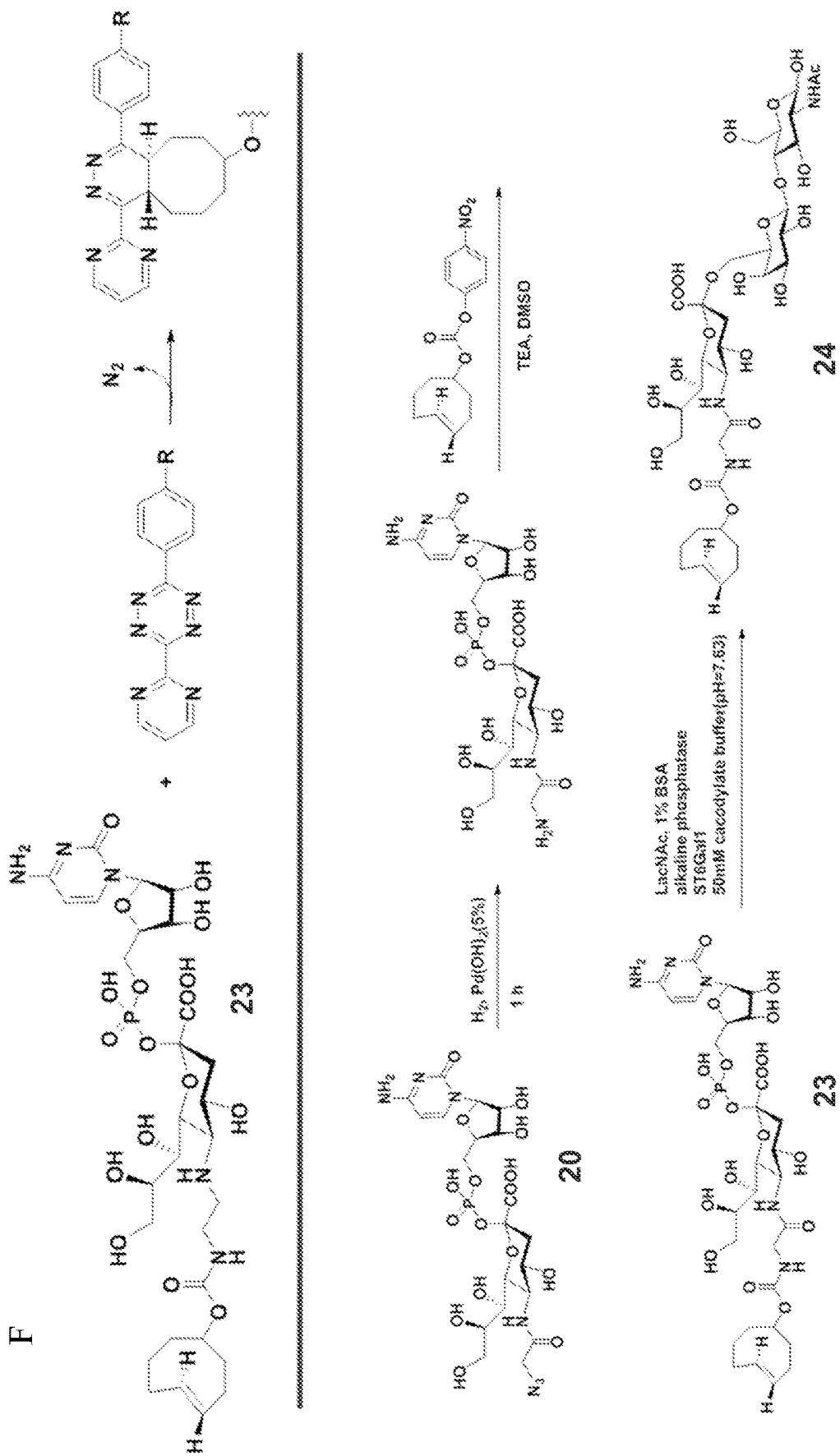

The present invention provides compounds, compositions, and methods useful for covalently linking an antibody, such as an IgG, or a fragment thereof, such as an Fc fragment, to a cargo molecule, such as a therapeutic or a diagnostic agent, through the use of click chemistry at a constituent glycan. More particularly, the invention involves the enzymatic attachment of a functionalized, terminal sialic acid to an N-linked glycan at one or more well-defined positions on the IgG heavy chain, which functionalized sialic acid serves as an acceptor site for subsequent attachment of the cargo molecule via a chemical click reaction. Advantageously, a preferred sialyltransferase, ST6Gal 1, is a robust enzyme that can be readily purified in large quantities. Optionally, invention involves additional enzymatic remodeling of the glycan to add a terminal galactose residue prior to attaching the sialic acid, in order to facilitate the enzymatic attachment of the functionalized sialic acid through the use of a sialyltransferase.

The chemoenzymatic method of the invention makes possible controlled attachment of the cargo molecule, such as a drug, to a specific site on the antibody or fragment thereof, yielding conjugates, for example antibody-drug conjugates (ADCs), with very little heterogeneity. Moreover, because the remodeling of the glycan prior to conjugation with the cargo is carried out post-translationally, any antibody or fragment thereof can be utilized. The method is modular; any antibody of choice can be remodeled to include a functionalized sialic acid that contains a clickable moiety, and this functionalized antibody can be paired with any desired cargo molecule (drug, label, and the like) that has been modified (functionalized) to include the partner moiety for the click reaction. Thus a wide variety of antibody-cargo combinations are possible, all utilizing the glycan remodeling and conjugation chemistries described herein, while varying the selection of antibody and/or cargo molecule. Useful click chemistries for conjugation can be found in U.S. Pat. No. 8,133,515, WO/2009/067663; additional methods and chemistries for conjugation include, but are not limited to, those described in US Pat. Publication 20120197012, issued as U.S. Pat. No. 8,012,322; WO/2012/047663 and US Pat. Publication 20130310570. It should be noted that the reactive functional groups involved in the antibody-cargo conjugation reaction can apportioned between the glycan and the cargo molecule in any convenient way. For example, in one embodiment, an antibody having a glycan that has been modified to contain an azide functional group can be reacted in a click reaction with a cargo molecule, e.g., a drug, that has been modified to contain dibenzylcyclooctynol (DIBO) to yield an antibody-drug conjugate; alternatively, the glycan of the antibody can be modified to contain a dibenzylcyclooctynol (DIBO) group, and the drug can be modified to contain the azide.

Additionally, antibody drug conjugates of the invention can be therapeutically multifunctional. For example, therapeutic antibodies that target cancer cells or bacterial pathogens with demonstrated therapeutic success can be further post-translationally engineered to carry a cytotoxic drug, for example, to further enhance their therapeutic efficacy. Moreover, as demonstrated in the Example below, the functionalized antibodies of the invention are expected to retain effector function, such as Fcγ Receptor binding, despite the conjugation of cargo, thereby further enhancing their utility.

The functionalized antibody of the invention thus preferably contains at least one glycan that has been remodeled to contain a functionalized sialic acid. Functionalized sialic acid is sialic acid with a functional group that can participate in covalent linkage with a functionalized cargo molecule, preferably through a click reaction. The invention also includes functionalized antibody fragments such as a heavy chain, an Fc region or a hinge Fc region, as well as other molecules that incorporate one or more of such fragments.

In a preferred embodiment, the functionalized antibody is covalently linked to a functionalized therapeutic agent to form an antibody drug conjugate (ADC). Because the method of the invention permits a greater degree of control over the specification of attachment sites of a therapeutic agent, it provides an improved means of creating ADCs with consistent pharmacokinetics. In addition, the method is highly efficient, does not require a toxic metal catalyst, and can be used to create ADCs with non-compromised FcγRIIIa binding.

In a preferred embodiment, the cargo molecule is linked to a glycan, typically a biantennary glycan, which is present in the functionalized antibody at residue 297 of the antibody's heavy chain (Asn297 also known as Asparagine 297 or N297) as defined by the Kabat numbering system (Kabat et al., Sequences of Proteins of Immunological Interest, Vol. 1, 5th Ed. U.S. Public Health Service, National Institutes of Health. NIH Publication No. 91-3242; Copyright 1991). Because antibodies contain two heavy chains, and the N-linked glycan as Asn297 is typically biantennary, the functionalized antibodies of the invention preferably contain 1, 2, 3, or 4 cargo molecules.

Antibody

The functionalized antibody of the invention may be a monoclonal or a polyclonal antibody. In a preferred embodiment, the functionalized antibody is a monoclonal antibody. In one aspect of the invention, the functionalized antibody recognizes a target antigen. In a preferred embodiment, the target antigen is a tumor antigen and is localized to a tumor cell's surface. In a further embodiment, the functionalized antibody bound to the target antigen can be internalized after binding to the tumor cell. Where the functionalized antibody is covalently linked to a cargo molecule, the cargo molecule can be released into the cell after internalization. For example, when the functionalized antibody is linked to a cytotoxic drug, the cytotoxic drug can be released into the cell after internalization, resulting in cell death. Preferably, the target antigen displays differential expression between normal cells and tumor cells, displaying increased expression on tumor cells. The target antigen can be a B cell antigen, for example CD19, CD20, CD21, CD22, CD79, or CD180, or a fragment thereof. The target antigen can be a protein elevated in certain types of cancers or a tumor marker, for example Her2, Muc16, MS1, prostate-specific membrane antigen (PSMA) or CD30, or a fragment thereof. The target antigen could alternatively be Glycoprotein NMB, CD33, CD56, CD66e/CEACAM5, CD74, CD79b, CD138, CA-IX, SLC44A4, Mesothelin, or Nectin-4, or a fragment thereof. The target antigen could be a tissue-specific marker or a glycan, or a fragment thereof. In one embodiment, the functionalized antibody binds to the target antigen with high affinity. In a preferred embodiment, the affinity of the functionalized antibody will be at least about 5 fold, preferably 10 fold, more preferably 25-fold, even more preferably 50-fold, and most preferably 100-fold or more, greater for a target molecule than its affinity for a non-target molecule.

The functionalized antibody or functionalized antibody fragment can be of any class, such as an IgM, IgA, IgD, IgE, or IgG class, or subclass of immunoglobulin molecule. In a preferred embodiment, the functionalized antibody or functionalized antibody fragment is of the IgG class. The functionalized antibody or functionalized antibody fragment can be from the IgG1, IgG2, IgG3, and/or IgG4 subclasses. In a preferred embodiment, the functionalized antibody or functionalized antibody fragment is from the IgG1 subclass. In a preferred embodiment, the functionalized antibody or functionalized antibody fragment has a conserved Asparagine at position 297 of the heavy chain as defined by the Kabat numbering system (Kabat et al., Sequences of Proteins of Immunological Interest, Vol. 1, 5th Ed. U.S. Public Health Service, National Institutes of Health. NIH Publication No. 91-3242; Copyright 1991).

The functionalized antibody or functionalized antibody fragment may be derived from a human, a mouse, a rat, or another mammal. The functionalized antibody or functionalized antibody fragment may also be a hybridization of antibodies from human, mouse, rat, and/or other mammals.

In a preferred embodiment, the functionalized antibody or functionalized antibody fragment is derived from a human. The functionalized antibody or functionalized antibody fragment may be produced by hybridoma cells or cell lines. The functionalized antibody or functionalized antibody fragment may be humanized.

The functionalized antibody may be a monoclonal antibody. Examples include, without limitation, brentuximab, inotuzumab, gemtuzumab, lorvotuzumab, glembatumumab, milatuzumab, labestuzumab, rituximab, trastuzumab, alemtuzumab, bevacizumab, cetuximab, panitumumab, ibritumomab, or tositumomab.

Antibodies suitable for post-translational functionalization according to the invention can be generated by a suitable method known in the art. For example, monoclonal antibodies can be prepared using a wide variety of techniques including, for example, the use of hybridoma, recombinant, and phage display technologies, or a combination thereof. Any technique which provides for the production of antibody molecule by continuous cell lines in culture may be used. For example, the hybridoma technique originally developed by Kohler and Milstein (256 Nature 495-497 (1975)) may be used. See also Asubel et al., Antibodies: a Laboratory Manual (Harlow & Lane eds., Cold Spring Harbor Lab. 1988); Current Protocols in Immunology (Colligan et al., eds., Greene Pub. Assoc. & Wiley Interscience 30 N.Y., 1992-1996).

Antibodies can be elicited in an animal host by immunization with a target antigen, or can be formed by in vitro immunization of immune cells. The antibodies can also be produced in recombinant systems in which the appropriate cell lines are transformed, transfected, infected or transduced with appropriate antibody-encoding DNA. Alternatively, the antibodies can be constructed by biochemical reconstitution of purified heavy and light chains.

In a preferred embodiment, the antibodies are human antibodies. Human antibodies can be made by a variety of methods known in the art including, for example, phage display methods using antibody libraries derived from human immunoglobulin sequences. In addition, commercial antibodies may be used to generate the antibodies of the invention. The antibody may be generated in humans, mice, or other mammals or mammalian systems using conventional means.

Once an antibody or antibody fragment has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences known in the art to facilitate purification.

Functionalized Antibody

The functionalized antibody preferably includes a functionalized sialic acid, which functionalized sialic acid has been covalently attached to a glycan of the antibody during the process of glycan remodeling.

The carbon numbering scheme for sialic acid is shown below:

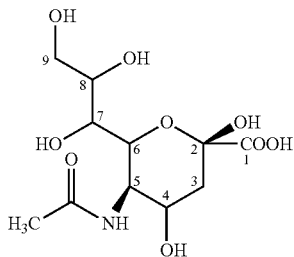 [SMILES: CC(=O)N[C@@H]1C(O)C[C@@](O)(C(=O)O)OC1C(O)C(O)CO]

Sialic acid (Sia) as the term is used herein can include N- or O-substituted derivatives of neuraminic acid, 2-keto-5-acetamido-3,5-dideoxy-d-glycero-d-galactononulosonic acid (Neu5Ac), and 2-keto-3-deoxy-d-glycero-d-galactononionic acid (KDN). For example, sialic acid and its derivatives can include and are sometimes referred to as N-Acetylneuraminic acid, NANA, NeuAc, Neu5Ac, or Neu5Gc.

Functionalized sialic acid as the term is used herein refers to a sialic acid having a functional group that participates in a covalent linkage with a functionalized cargo molecule. The sialic acid functional group serves as the site for the covalent linkage of the cargo molecule to the antibody.

In one embodiment, the functional group is positioned at C-9 of the sialic acid (see, e.g., compound 1 in FIG. 1B). In another embodiment, the functional group is positioned at C-5 of the sialic acid (see, e.g., the compounds shown in FIG. 1C). Functionalized sialic acid can contain one, two or more functional groups capable of covalent linkage with a cargo molecule, positioned at C-9, C-5 or any other suitable position on the sialic acid, such as, without limitation, C-1, C-2, C-4, C-7, or C-8. A functionalized sialic acid containing more than one functional group may contain the same or different functional groups.

Exemplary functional groups include azide, nitrone, nitrile oxide, azoxy, diazo, acyl diazo, and trans-cyclooctene; preferably, the functional group or groups present on the functionalized sialic acid allow for the covalent attachment of a cargo molecule via click chemistry. Exemplary suitable chemistries are described in U.S. Pat. No. 8,133,515, WO/2009/067663; additional methods and chemistries for conjugation include, but are not limited to, those described in US Pat. Publication 20120197012, issued as U.S. Pat. No. 8,012,322; WO/2012/047663 and US Pat. Publication 20130310570. In a preferred embodiment, the functionalized antibody includes an azido-modified sialic acid. An exemplary functionalized sialic acid is 5-acetamido-9-azido-3,5,9-tri-deoxy-β-D-glycero-D-galacto-2-nonulopyranosylonic acid (Neu5Ac9N3). (Mbua et al., Angewandte Chemie, 2013, 52(49):13012-13015).

Human IgG is typically characterized by glycosylation at position Asn297 (numbering according to Kabat) in the heavy chain CH2 region of the Fc region (see FIG. 1A). Accordingly, in a preferred embodiment, the functionalized antibody is functionalized at one or more oligosaccharides attached to an asparagine, preferably Asn297. In a preferred functionalized antibody, a functionalized sialic acid is present at the terminus of one or more oligosaccharides (and/or, in the case of a bi- or tri-antennary oligosaccharide, one or more arms thereof) attached to Asn297 of the functionalized antibody's heavy chain. Control over the site of antibody functionalization provides an improved means of creating conjugated antibodies with consistent properties and ADCs with consistent pharmacokinetics.

The terminal, functionalized sialic acid is preferably attached to a penultimate galactose moiety on the glycan. If the glycan (prior to sialylation) does not terminate with galactose, for example if it terminates with N-acetylglucosamine (GlcNAc), the glycan is preferably enzymatically remodeled, as detailed herein, to add a terminal galactose prior to adding a terminal sialic acid, with the galactose eventually assuming the penultimate position after sialylation.

It should be noted that antibodies can be genetically engineered to include nonnative glycosylation sites. Thus present invention includes not only antibodies having functionalization (via glycan remodeling) at native Asn297 of human IgG (or its counterparts in other mammalian systems) but also those that have been remodeled at nonnative glycosylation sites to yield functionalized N-linked oligosaccharides having a functionalized terminal sialic acid as described herein.

Antibody-Cargo Conjugate

The invention further provides a conjugate that includes the functionalized antibody and a cargo molecule, covalently linked at the sialic acid of the remodeled glycan. The cargo molecule can be, without limitation, a cytotoxic drug, a cytostatic agent, a toxin, a radioisotope or radionuclide, a nucleotide, an RNA, a DNA, an antibiotic, an immunosuppressive agent, a fluorophore, a dye, and/or a protein. The cytotoxic drug can be a microtubule inhibitor and/or a DNA-damaging agent. A microtubule inhibitor can be an auristatin or a maytansinoid. A DNA-damaging agent can be anthracycline, calicheamicin, duocarmycin, or pyrrolobenzodiazepine. In one embodiment, the cytotoxic drug can be doxorubicin. Additionally or alternatively, the cytotoxic drug can be from the dolastatin family; a pyrrolobenzodiazepine (PBD); a polymerase inhibitor, for example, α-amanitin; ozogamicin; mertansine; vedotin; or emtansine. The cargo can be biotin 8, FITC 9, or doxorubicin 10.

In one embodiment, a cargo molecule is linked to each of the four terminal ends of the antibody's two biantennary glycans at position 297 of the heavy chain. In another embodiment, the cargo molecule is linked to one, two, or three of the terminal ends of the antibody's glycans. In one embodiment, the same cargo molecule is linked to each of the antibody's glycan chains. In another embodiment, different cargo molecules may be linked to individual glycan chains on the same antibody.

The cargo molecule can naturally include or can be modified to include a functional group that reacts with a functionalized antibody. More particularly, where the conjugation reaction proceeds by way of a click reaction, the cargo includes the partner reactive moiety that allows it to participate in the click reaction with the functionalized antibody. In a preferred embodiment, the cargo molecule includes or can be modified to include a functional group that reacts with an azido group on the functionalized sialic acid of the functionalized antibody. In one embodiment, the cargo molecule is modified to include dibenzylcyclooctynol (DIBO); the functionalized cargo molecule can include a label, a fluorophore, or a drug, such as DIBO-biotin 8, DIBO-FITC 9, or DIBO-doxorubicin 10.

The functionalized cargo molecule is ultimately covalently linked to the functionalized antibody or antibody fragment of the invention to yield the conjugate of the invention, such as an antibody-drug conjugate (ADC). The cargo molecule can be conjugated to the functionalized antibody enzymatically, chemically, or chemoenzymatically. In a preferred embodiment, the cargo is conjugated to the antibody chemically. In one embodiment of the invention, the cargo is conjugated to the antibody via click reactions. For example, the cargo can be conjugated to the antibody via Staudinger ligation using modified phosphines or copper(I)-catalyzed cycloaddition with terminal alkynes (CuAAC). In a preferred embodiment, the cargo is conjugated to the antibody by strain-promoted alkyne-azide cycloaddition (SPAAC). This conjugation proceeds by way of azido/alkyne click chemistry and, when the cargo molecule is modified by DIBO as shown in the Example, may result a heterocyclic conjugate, such as a triazole conjugate.

It should be further noted that invention envisions and includes antibody-cargo conjugates that contain dendrimers and dendritic scaffolding. Appelhans et al., for example, have described dendritic glycopolymers based on dendritic polyamine scaffolds (Chem. Soc. Rev. 2015, Advance Article DOI:10.1039/C4CS00339J) In the present invention, cargo molecules, such as drug molecules, are attached to the dendrimer termini, rather than carbohydrates.

Optional Linker Region

Optionally, the cargo molecule can include a linker region. In one embodiment, the linker region may be non-cleavable. In another embodiment, the linker region may be degradable or cleavable. In a preferred embodiment, the linker region can include an acid-labile region which becomes unstable and degrades at low pH, including, for example, the pH of a lysosome. For example, in one embodiment, an acid-sensitive hydrazine linker may be added between the functional group and the cargo. An exemplary functionalized cargo molecule that includes a linker region is [DIBO]-[an acid-sensitive hydrazine linker]-[cytotoxic drug]. In another embodiment, the linker can include a redox-active group such as a disulfide, which can be cleaved, for example, by reduction to thiol. In another embodiment, the linker region can include a protease-cleavable region. In yet another embodiment, the linker region can include a disulfide region. Typically, the optional linker region is positioned between the functional group that reacts with the sialic acid (e.g., the click reaction partner, such as the alkyne) and the cytotoxic drug, label, etc. It should be noted that the linker region can include the functional group that reacts with the sialic acid on the antibody.

Optionally, the functionalized antibody, antibody fragment, or conjugate of the invention can be labeled. Examples of labels include but are not limited to radioactive nucleotides ($^{125}I$, $^{3}H$, $^{14}C$, $^{32}P$), chemiluminescent, fluorescent, or phosphorescent compounds (e.g., dioxetanes, xanthene, or carbocyanine dyes, lanthanide chelates), particles (e.g., gold clusters, colloidal gold, microspheres, quantum dots), and/or enzymes (e.g., peroxidases, glycosidases, phosphatases, kinases).

Chemoenzymatic Synthesis of Functionalized Antibody

Antibodies having the same protein sequence can be differentially glycosylated depending on many factors such as their environment, source, purification and storage conditions, etc. As shown in FIG. 1A, a typical glycan at position Asn297 of human IgG contains a biantennary heptasaccharide core with extensions that are variable. Each arm of the biantennary heptasaccharide core terminates with a N-acetylglucosamine (GlcNAc) residue; if there is no extension, that glycoform is commonly referred to as a "G0" glycoform. If one of the arms is extended by a terminal galactose (Gal) residue, the glycoform is referred to as "G1"; likewise, if both arms are extended by terminal galactose residues, the glycoform is referred to as "G2". For example, naturally occurring human IgG may contain a mixture of glycoforms at Asn297. In Example I, for instance, it was found that IgG antibodies possessing biantennary N-glycans at Asn297 included a mixture of G0, G1, and G2 glycoforms.

The invention provides a method of making a functionalized antibody by enzymatically remodeling its glycans. The goal of glycan remodeling is to install a functionalized sialic acid on one or more glycan termini. A preferred enzyme for sialylation (i.e., a sialyltransferase) is one that utilizes galactose as a preferred substrate. If the antibody contains G0 and G1 glycoforms (terminating with GlcNAc), it may be desirable (yet optional) prior to sialylation, to enzymatically add galactose residues so as to increase the amount of G2 glycoform, thereby increasing the number of sites available for sialylation. Optionally, therefore, in order to provide as many terminal galactose residues as possible, the antibody is first subjected to an enzymatic galactosylation reaction to increase the number of terminal galactose residues (i.e., sites for sialylation), followed by sialylation with the functionalized sialic acid.

Additionally, if the antibody prior to remodeling contains an undesirable number of terminal sialic acid residues (see FIG. 1A) the method optionally involves enzymatically cleaving the preexisting, nonfunctionalized sialic acid residues prior to optional galactosylation, followed by sialylation with the functionalized sialic acid.

Sialylation

In one embodiment, the antibody or fragment thereof is contacted by at least one sialyltransferase, under conditions and for a time sufficient to incorporate at least one functionalized sialic acid onto the terminus of at least one glycan of the antibody. It should be noted, as discussed in the Example, that reaction conditions can be altered so as to achieve mono-sialylation or bis-sialylation of the biantennary glycans, as desired. Thus, adjusting the reaction conditions for the sialylation reaction (e.g., increasing or decreasing the time of the reaction) allows for tuning of the number of functionalized sialic acids per antibody and, in turn, allows tuning of the number of cargo molecules carried per antibody.

The antibody and a sialic acid substrate, such as a functionalized CMP-sialic acid or derivative thereof, can be contacted by at least one sialyltransferase under conditions and for a time sufficient to incorporate one or two functionalized sialic acids onto a glycan of the antibody, preferably onto the biantennary glycans at position 297. The sialyltransferase may be derived from mammals, fishes, amphibians, birds, invertebrates, or bacteria. In one embodiment, the sialyltransferase is an α-(2,3)-sialyltransferase. In another embodiment, the sialyltransferase is an α-(2,6)-sialyltransferase. In yet another embodiment, the sialyltransferase is an α-(2,8)-sialyltransferase. In a preferred embodiment, the sialyltransferase is an α-(2,6)-sialyltransferase, preferably a β-galactoside α-(2,6)-sialyltransferase 1 (ST6Gal 1). In a preferred embodiment, the sialyltransferase is a mammalian sialyltransferase. In other embodiments, the sialyltransferase rat 3-galactoside α-2,6-sialyltransferase 1 (ST6Gal 1); *Pasteurella multocida* α-(2,3)-sialyltransferase; or CMP-N-acetylneuraminate-β-galactosamide-α-2,3-sialyltransferase (ST3Gal IV).

The functionalized sialic acid substrate is typically a nucleotide associated sialic acid, preferably a CMP-sialic acid, which is also known as CMP-Sia. In a preferred embodiment, the functionalized CMP-sialic acid is a CMP-azido-modified sialic acid, more preferably CMP-Neu5Ac9N3. In a particularly preferred embodiment, the antibody is contacted with CMP-sialic acid derivative 1 in the presence of ST6Gal 1.

Surprisingly, it was found that naturally occurring sialyltransferases were able to catalyze sialylation of the glycan using functionalized sialic acid-CMP derivative as a substrate. Sialic acid derivatives that were functionalized at either the C-9 position or the C-5 position (see, e.g., FIG. 1) were well tolerated by ST6Gal1, for example, making the remodeled, functionalized antibodies very accessible synthetically. Boeggeman et al. have described galactosylating a G0 glycoform with a modified galactose having a chemical handle at the C2 position; however, the use of a mutant β1,4-galactosyltransferase was required to incorporate the modified galactosides (Bioconjug. Chem. 2009, 20(6):1228-36), and modified enzymes are frequently difficult to express. Additionally, terminal galactosides on antibodies are less desirable because they are recognized by liver receptors that may take the antibodies out of circulation. Moreover, ketones are not attractive for ligations; reactions are slow and often a large excess of reagent is required to drive the reactions to completion.

The ability to use naturally occurring enzymes in various embodiments of the present invention to incorporate functionalized sialic acids allows for a simpler and more efficient chemoenzymatic synthesis. Moreover, in the present invention, as noted elsewhere herein there is flexibility in attachment of different numbers of the cargo molecule, by varying the conditions of the enzymatic reaction. For example, short treatment with ST6Gal 1 results in the incorporation of one modified sialoside per glycan, whereas longer exposure gives two sialosides per glycan.

Galactosylation

Optionally, prior to sialylating the antibody or fragment thereof, the method for making the functionalized antibody or fragment includes enzymatically remodeling the antibody or fragment so that the glycan(s) contain terminal galactose and thereby can serve as a better substrate for sialyltransferases such as a β-galactoside α-(2,6)-sialyltransferase 1 (ST6Gal 1). For example, the naturally occurring glycan may terminate with GlcNAc, which is not a preferred substrate for ST6Gal 1. The antibody or fragment is thus optionally contacted with UDP-galactose (UDP-Gal) and galactosyltransferase (GalT) under conditions and for a time sufficient to achieve galactosylation of one or both arms of the N-glycan of residue 297 of the antibody's heavy chain (Asn297). In a preferred embodiment, an antibody can be contacted with galactosyltransferase (GalT) and UDP-Gal under conditions and for a time sufficient to enable galactosylation of both arms of each N-glycan of residue 297, creating the maximum number of acceptor sites for sialyl transferase.

It should be noted that if a sialyltransferase that has a different specificity is utilized, for example one that preferentially attaches sialic acid to, for example, GlcNAc, then the remodeling chemistry is adjusted to produce antibody intermediates that have GlcNAc as their glycan terminal residues.

Also optionally, prior to sialylation or galactosylation, the antibody or fragment thereof can be de-sialylated to remove non-functionalized sialic acid residues, for example by contacting the antibody or fragment thereof with a sialidase or neuraminidase, such as an α-2,6-sialidase (see FIG. 1A).

The functionalized antibody may, or may not, contain a fucose as part of the core glycan structure at residue 297 (see, e.g., FIG. 1A showing a fucose as part of the glycan). Optionally, the antibody can be treated with a fucosidase or a fucosyl transferase to remove or add a fucose residue, as desired.

Conjugation

To make the conjugate of the invention, the functionalized antibody or fragment is contacted with a functionalized cargo molecule under conditions and for a time sufficient for a covalent linkage to form between the functionalized antibody and the functionalized cargo molecule. In a preferred embodiment, conjugation is achieved through a chemical reaction, such as through click chemistry, preferably metal-free click chemistry as described herein. For example, a functionalized antibody or fragment thereof, which has been modified to incorporate a 1,3-dipole-functional moiety (e.g., a azide functional moiety) can be reacted with certain alkynes in a cyclization reaction to form heterocyclic compounds. Suitable alkynes (e.g., strained, cyclic alkynes) that can be used to functionalize the cargo molecule, and methods of making such alkynes are described in, for example, U.S. Pat. No. 8,133,515; additional methods and chemistries for conjugation include, but are not limited to, those described in US Pat. Publication 20120197012, issued as U.S. Pat. No. 8,012,322; WO/2012/047663 and US Pat. Publication 20130311570.

In an exemplary embodiment, a functionalized antibody or fragment containing an azido-modified terminal sialic acid, and functionalized cargo molecule such as a dibenzyl-cyclooctynol (DIBO)-derivative covalently linked to a cytotoxic drug, a toxin, a radioisotope or radionuclide, a nucleotide, an RNA, a DNA, an antibiotic, a fluorophore, a dye, and/or a protein, are reacted under conditions and for a time to yield the desired antibody-cargo conjugate. For example, DIBO can be conjugated to biotin 2, FITC 3, or doxorubicin 4. Alternatively, the conjugation reaction can be based on other chemistries, for example click chemistries involving functional groups such as, nitrone, nitrile oxide, azoxy, diazo, acyl diazo, and trans-cyclooctene.

Compositions and Methods of Use

Also included in the invention is a method for treating or preventing various diseases, including cancer, by administration of a functionalized antibody. The cancer can be a carcinoma of the bladder, breast, cervix, colon, endometrium, kidney, lung, esophagus, ovary, prostate, pancreas, skin (i.e. melanoma), stomach, and/or testes.

In one aspect, the cancer is positive for the target antigen recognized by the therapeutic antibody. In a preferred embodiment, the target antigen is preferentially expressed on the cancer. In a preferred embodiment, the functionalized antibody will bind to the cells of the cancer and be endocytosed.

In one aspect, one or more functionalized antibodies are administered alone or in combination with one or more additional therapeutic compounds or treatments. In one embodiment, an effective amount of the functionalized antibody is administered to a patient. In a preferred embodiment, an effective amount of the functionalized antibody conjugated to a cytotoxic drug is administered to a patient. In another embodiment, a functional amount of the functionalized antibody and a chemotherapeutic agent or anticancer agent is administered to a patient. Suitable anticancer agents include, but are not limited to methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, Cytoxan, etoposide, 5-fluorouracil, BCNU, irinotecan, camptothecins, bleomycin, doxorubicin, idarubicin, daunorubicin, dactinomycin, plicamycin, mitoxantrone, asparaginase, vinblastine, vincristine, vinorelbine, paclitaxel, calicheamicin, and docetaxel.

The functionalized antibody can be in the form of a pharmaceutical composition for administration that is formulated to be appropriate for the selected mode of administration, and pharmaceutically acceptable diluent or excipients, such as buffers, surfactants, preservatives, solubilizing agents, isotonicity agents, stabilizing agents, carriers, and the like.

Various delivery systems are known and can be used to administer a functionalized antibody, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The functionalized antibody may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the functionalized antibody of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In one embodiment, it may be desirable to administer the functionalized antibody of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, or fibers. In one embodiment, administration can be by direct injection into colorectal tissue or at the site (or former site) of a malignant tumor or neoplastic or pre-neoplastic tissue.

EXAMPLES

The present invention is illustrated by the following examples. It is to be understood that the particular examples, materials, amounts, and procedures are to be interpreted broadly in accordance with the scope and spirit of the invention as set forth herein.

Example 1

Preparation of Well-Defined Antibody-Drug Conjugates Through Glycan Remodeling and Strain Promoted Azide-Alkyne Cycloaddition Typically, cytotoxic drugs are linked to antibodies by electrophilic modification of lysine or cysteine residues using N-hydroxysuccinimide ester or maleimide-activated drugs, respectively.[2] These conjugation methods lack selectivity and give heterogeneous mixtures of products that differ in the sites and stoichiometry of modification. These parameters have a significant impact on the pharmacokinetic properties of ADCs and therefore there is an urgent need for the development of site-specific conjugation methodologies. Homogeneous ADCs have been obtained by genetic engineering of antibodies to incorporate additional cysteines,[4] unnatural amino acids[5] or tags for transamination reactions.[6] These approaches have provided ADCs that have improved therapeutic and pharmacokinetic properties in animal models highlighting the importance of site-specific conjugation methodologies.[7]

Each heavy chain of an IgG antibody is modified at Asn297 with a complex biantennary N-linked oligosaccharide (see FIG. 1A), which does not affect antigen binding but influences effector functions such as complement activation and antibody-dependent cellular cytotoxicity (ADCC).[8] We envisaged that enzymatic remodeling of the oligosaccharide of an antibody would provide an opportunity to introduce reactive groups that can be exploited for the site-specific attachment of a cytotoxic drug. The premise of such an approach is based on the observation that glycosyl transferases often tolerate chemical modifications in their sugar nucleotide substrates, allowing the installation of reactive functionalities such as ketones, alkynes or azides.[9] The incorporation of an azide was expected to be particularly attractive for drug attachment because this functionality is virtually absent in biological systems,[10] and can efficiently be reacted by Staudinger ligation using modified phosphines,[11] copper(I)-catalyzed cycloaddition with terminal alkynes (CuAAC),[12] or by strain-promoted alkyne-azide cycloaddition (SPAAC).[13] These conjugation methods, which are also referred to as click reactions, were expected to be more efficient than the conventionally used electrophilic conjugation methods for ADC preparation.

Thus, we set out to remodel the oligosaccharides of an anti-CD22 monoclonal antibody (Molina, *Annu Rev. Med.* 2008 59:237-250) and a control polyclonal antibody using CMP-sialic acid derivative 1 which has an azide at C-9 of the sialic acid moiety (FIG. 1B). See Li et al., *Angew. Chem.*

*Int. Ed.* 2014, 53, 7179-7182. This modification is tolerated by several sialyl transferases,[14] and it was expected that the azido moieties of the glycans of the resulting antibodies could then be reacted by SPAAC using dibenzylcyclooctynol (DIBO)[15] modified by for example biotin (2), FITC (3) or a cytotoxic drug such as doxorubicin (4). See also U.S. Pat. No. 8,133,515 and PCT publication WO/2009/067663. Modification of the antibodies with biotin or FITC made it possible to visualize the modification and conjugation with doxorubicin (Dox) gave an ADC that could be examined for cytotoxicity.

Figure 2:
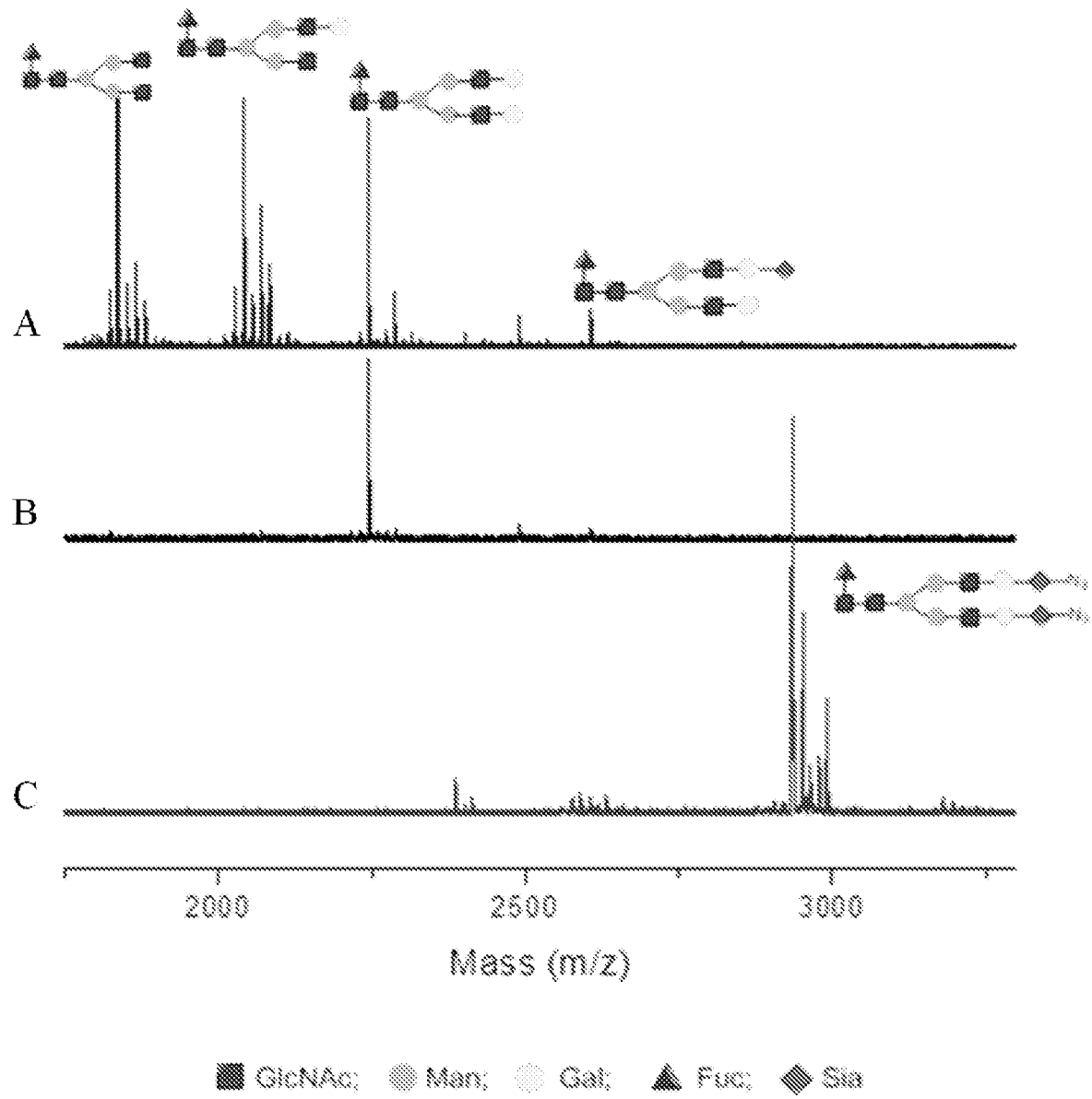
FIG. 2 shows mass spectrometry-based determination of glycan structures. (A) N-glycans isolated from the immunoglobulin G. (B) galactosylation of the IgG result in primarily digalactosylated glycan. (C) galactosylation followed by sialylation of the IgG using ST6Gal I results in primarily bisialylated glycan. Residues are denoted by symbols: N-acetylneuraminic acid (purple/dark gray diamond), galactose (yellow/light gray circle), N-acetylgalactosamine (yellow/light gray square, N-acetylglucosamine (blue/dark gray square), mannose (green/dark gray circle), and fucose (red/dark gray triangle).

Efficient remodeling of the glycans of antibodies with azido containing sialic acid requires a detailed knowledge of their compositions. Therefore, the control antibody was proteolyzed using trypsin and the generated glycopeptides treated with peptide N-glycosidase F (PNGase F) to release the oligosaccharide from the peptide, which was followed by permethylation and analysis of the resulting compounds by mass spectrometry. Mainly core fucosylated G0, G1 and G2 glycoforms were present with only a trace amount of a sialylated structure (FIG. 2A). To create the maximum number of acceptor sites for a sialyl transferase, the antibody was treated with galactosyl transferase (GalT) and UDP-Gal in the presence of calf intestine alkaline phosphatase (CIAP). Glycan analysis of the resulting antibody showed the presence of almost exclusively the G2 glycoform (FIG. 2B). Next, azido-modified sialic acid was incorporated by treatment with CMP-sialic acid derivative 1 in the presence of recombinant ST6Gal 1 and CIAP. After a reaction time of 24 h, glycan analysis showed mainly the formation of a mono-sialylated structure, which is in agreement with a previous study[16] that demonstrated that the α1,3Man-β1,2-GlcNAcβ1,4-Gal arm of a bi-antennary glycan of an IgG antibody is more accessible than the other arm for enzymatic remodeling. It was, however, found that prolonged exposure of the antibody to compound 1 and ST6Gal 1 resulted in near quantitative bis-sialylation (FIG. 2C). Treatment of the remodeled antibody with aqueous acetic acid (2 M) at 80° C. followed by analysis with high pH anionic exchange chromatography (HPAEC) showed that an average of 4.3 azido-containing sialic acids per antibody were present (Table 1).

TABLE 1

The number of N3 per glycoprotein quantified by various methods

| Methods | Number of $N_3$ per IgG | Number of $N_3$ per CD22 |
| --- | --- | --- |
| HPAEC | 4.3± | |
| MALDI | 4~4.5 | |
| FITC conjugate | 4.5± | |
| Doxorubicin conjugate | 4.1± | 3.5 |

Figure 3:
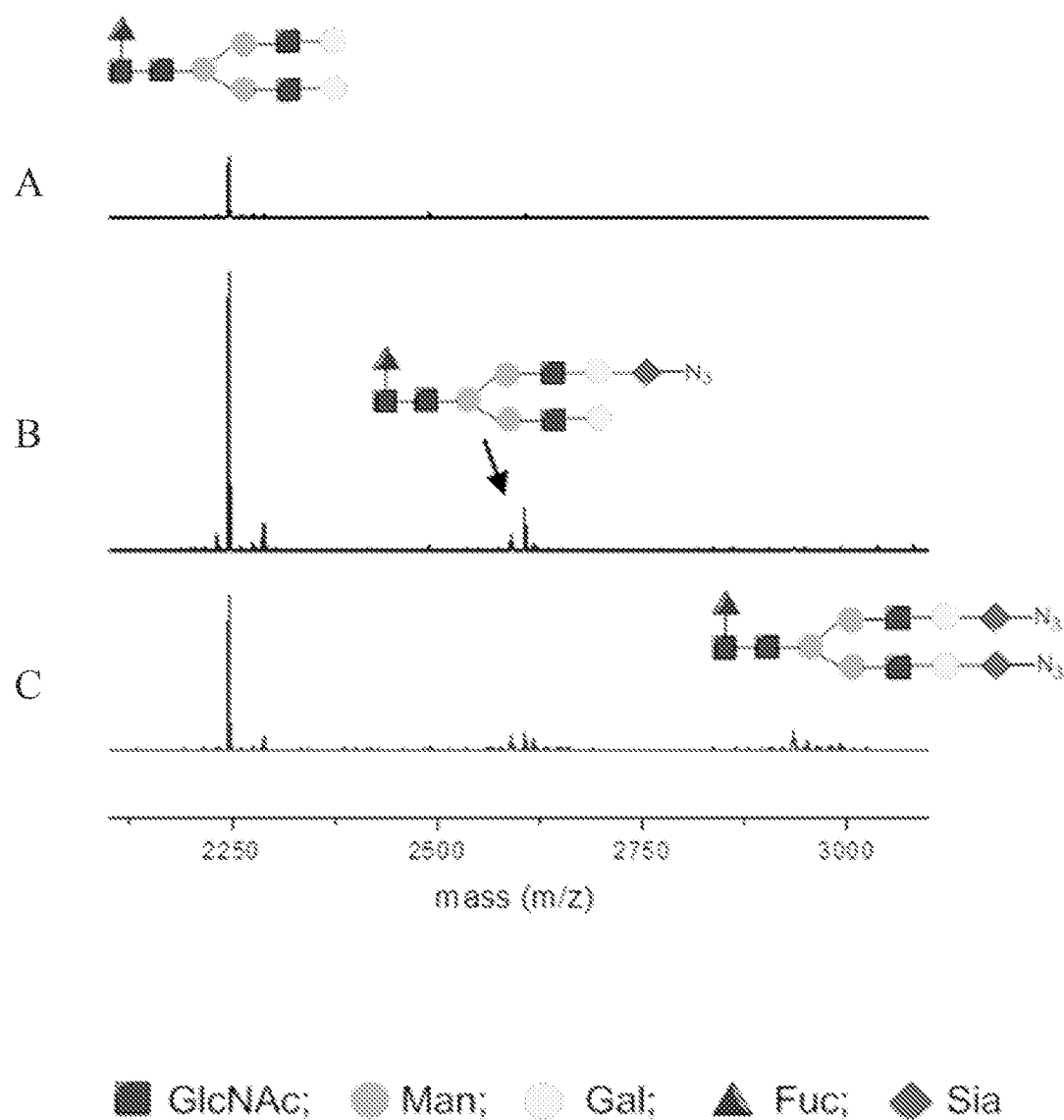
FIG. 3 shows mass spectrometry-based determination of glycan structures of IgG Galactosylation followed by sialylation using the other two sialyltransferases at 96 h: (A) IgG before further sialylation; (B) Sialylation by α-2,3-Sialyltransferase from *Pasteurella multocida* purchased from Sigma; (C) Sialylation by ST3Gal IV. Only small portion of digalactosylated glycan was converted to sialylated glycan.

The use of α-(2,3)-sialyltransferase of *Pasteurella multocida*[17] or ST3Gal IV resulted only partial modification even after extended incubations times highlighting the favorable properties of ST6Gal 1 (FIG. 3).

Figure 4:
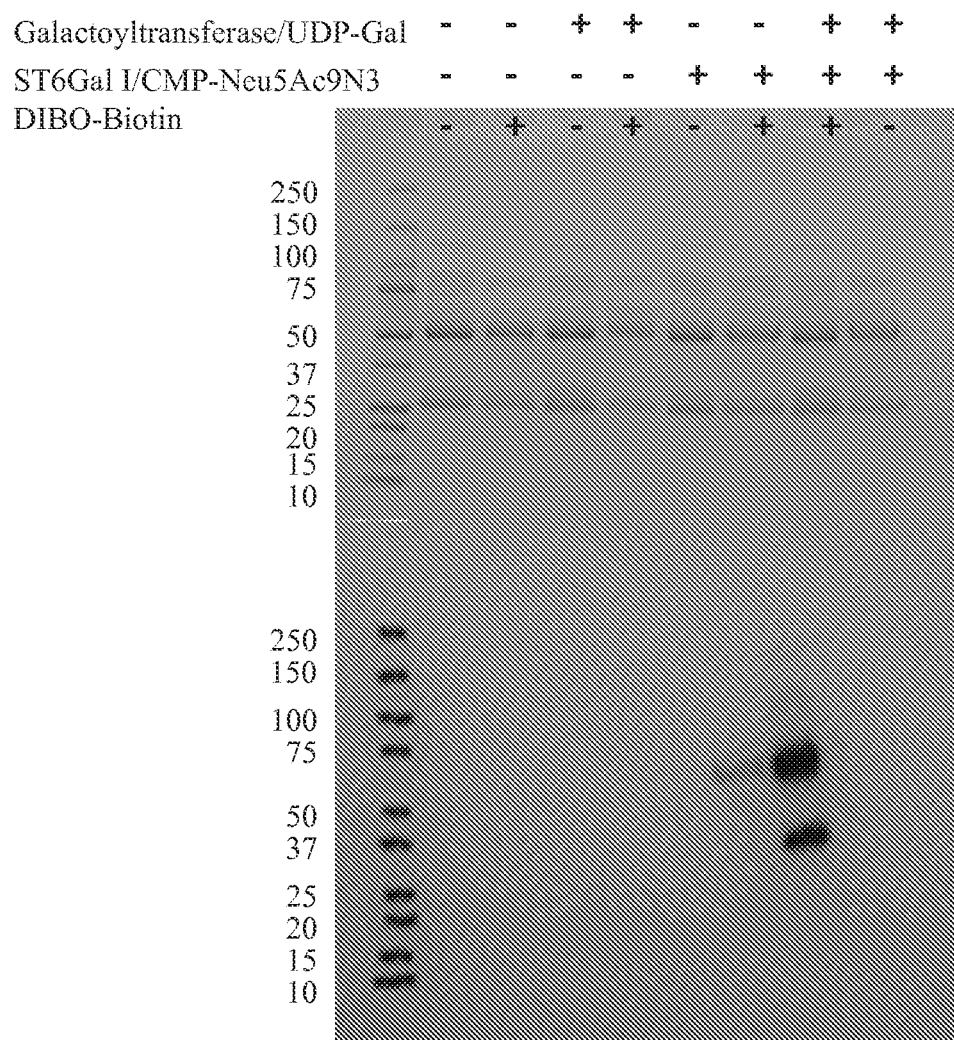
FIG. 4 shows confirmation of IgG labeling of CMP-Neu5Ac9N3 by ST6Gal I before and after remodeling with fully terminal galactose. Denature SDS-PAGE and the blot was probed with an HRP-conjugated anti-biotin antibody (bottom image). Total protein loading was confirmed through blue staining (top image).
Figure 5:
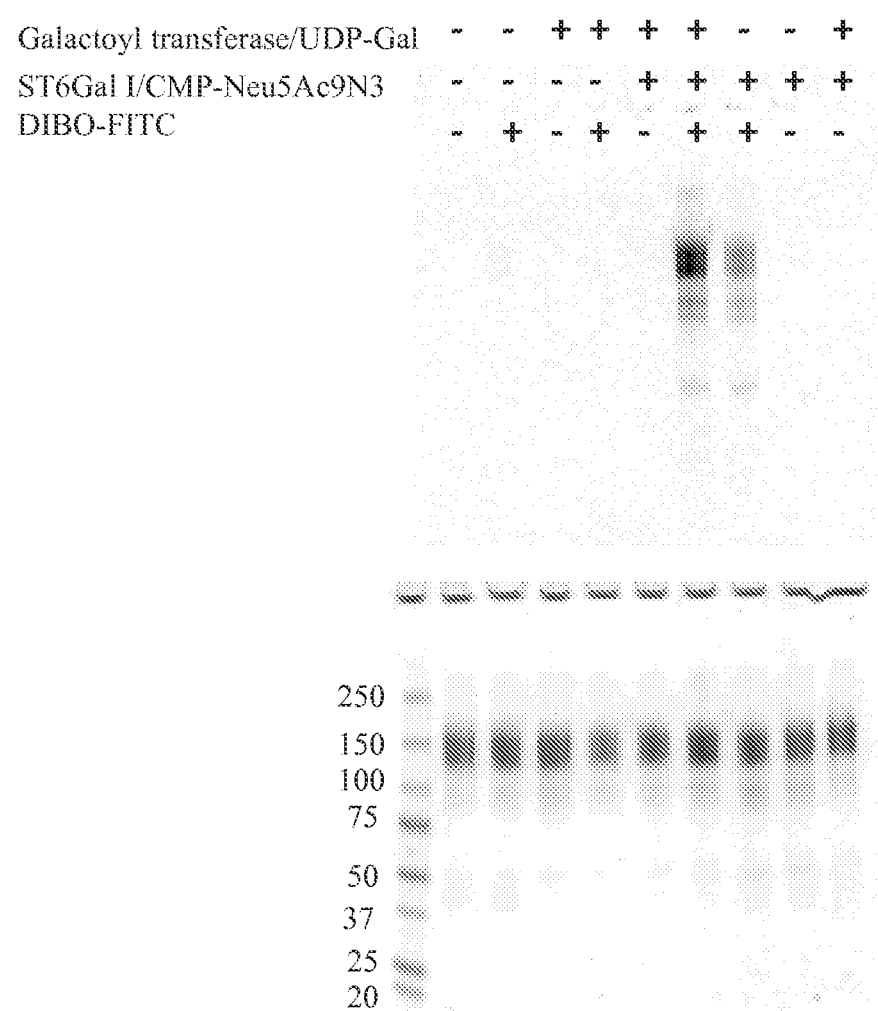
FIG. 5 shows confirmation of IgG labeling of CMP-Neu5Ac9N3 by ST6Gal I before and after remodeling with fully terminal galactose. Native SDS-PAGE, fluorescent scanning (top image); total protein loading was confirmed through blue staining (bottom image).
Figure 6:
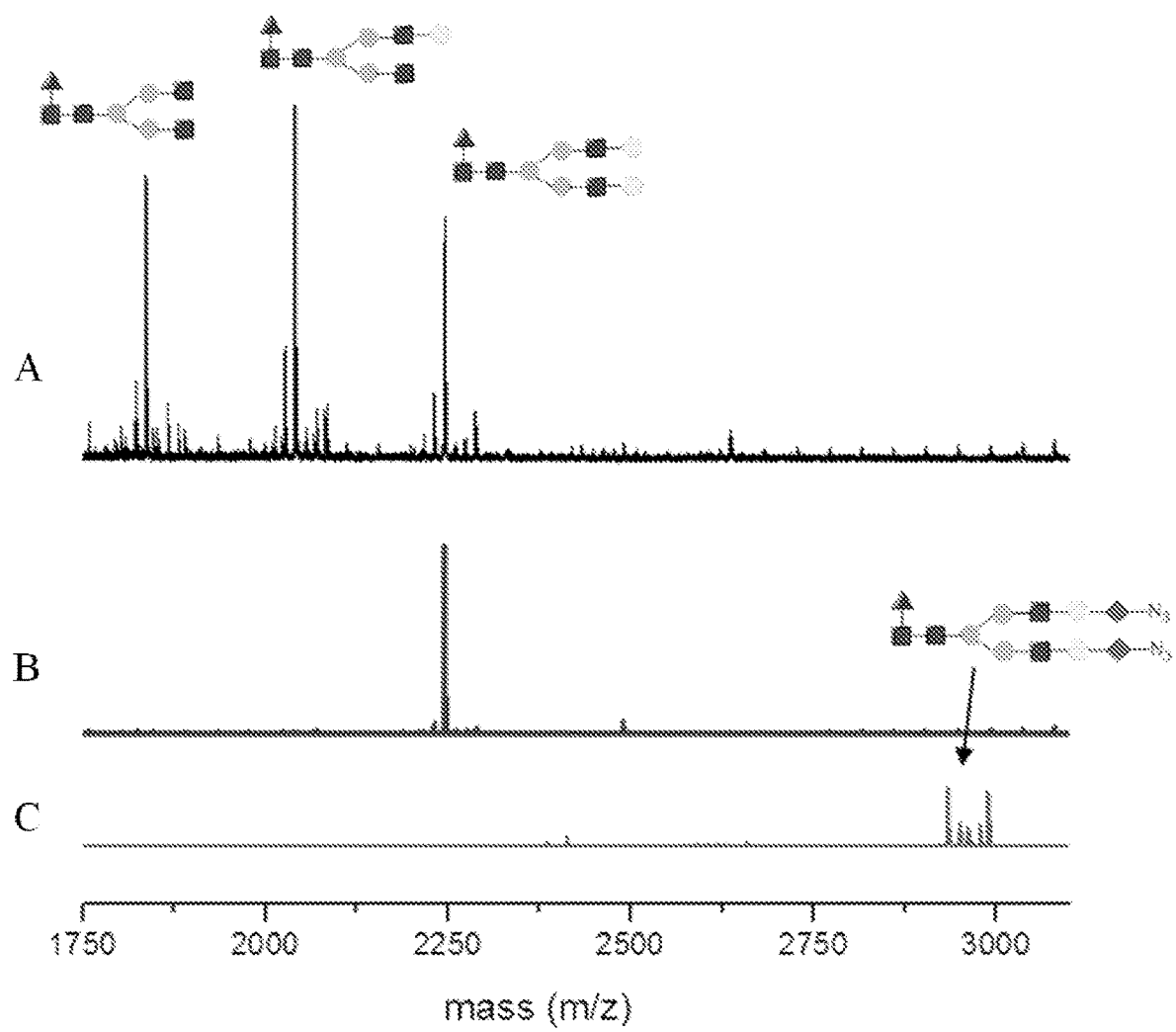
FIG. 6 shows mass-assisted laser-desorption/ionization time-of-flight mass spectroscopy (MALDI/TOF-MS) of N-glycan release from the anti-CD22 before and after remodeling with galactosyl transferase and sialyltransferase. (A) anti-CD22, no sialylated glycan was observed. (B) Galactosylation of the anti-CD22 results in primarily digalactosylated glycan. (C) Galactosylation followed by sialylation of the anti-CD22 using ST6Gal I results in full bisialylated glycan.

Having successfully remodeled the glycans of the antibody with azido-modified sialic acid, attention was focused on conjugation with DIBO-derivative 2 containing biotin. Thus, the remodeled antibody was exposed to 2 in cacodylate buffer (pH 7.6) for 2 h followed by purification using spin-filtration (10 KDa). SDS-PAGE of the resulting antibody followed by blotting and probing with an anti-biotin antibody conjugated to HRP (FIG. 4) resulted in two bands at 37 and 60 kDa, corresponding to labeling of the light and heavy chain, respectively. A similar labeling protocol using DIBO-FITC (3) followed by fluorescence intensity measurements demonstrated the presence of 4.5 fluorophores per antibody molecule, which is in agreement with the HPAEC analysis. Examination of the antibodies by native gel electrophoresis demonstrated a major band at 150 kDa, which exhibited fluorescence only after remodeling with ST6Gal I and compound 1 and expose to FITC-DIBO (3) (FIG. 5). Collectively, the results show that in addition to an N-glycan at Asn297, the light chain of the control antibody is partially modified by a glycan explaining the larger than four glycans per antibody molecule. The anti-CD22 antibody was remodeled in a similar fashion and in this case no glycosylation of the light chain was observed (FIG. 6). Furthermore, the various experiments show that the labeling procedure is highly selective for azido-modified antibodies.

Figure 7:
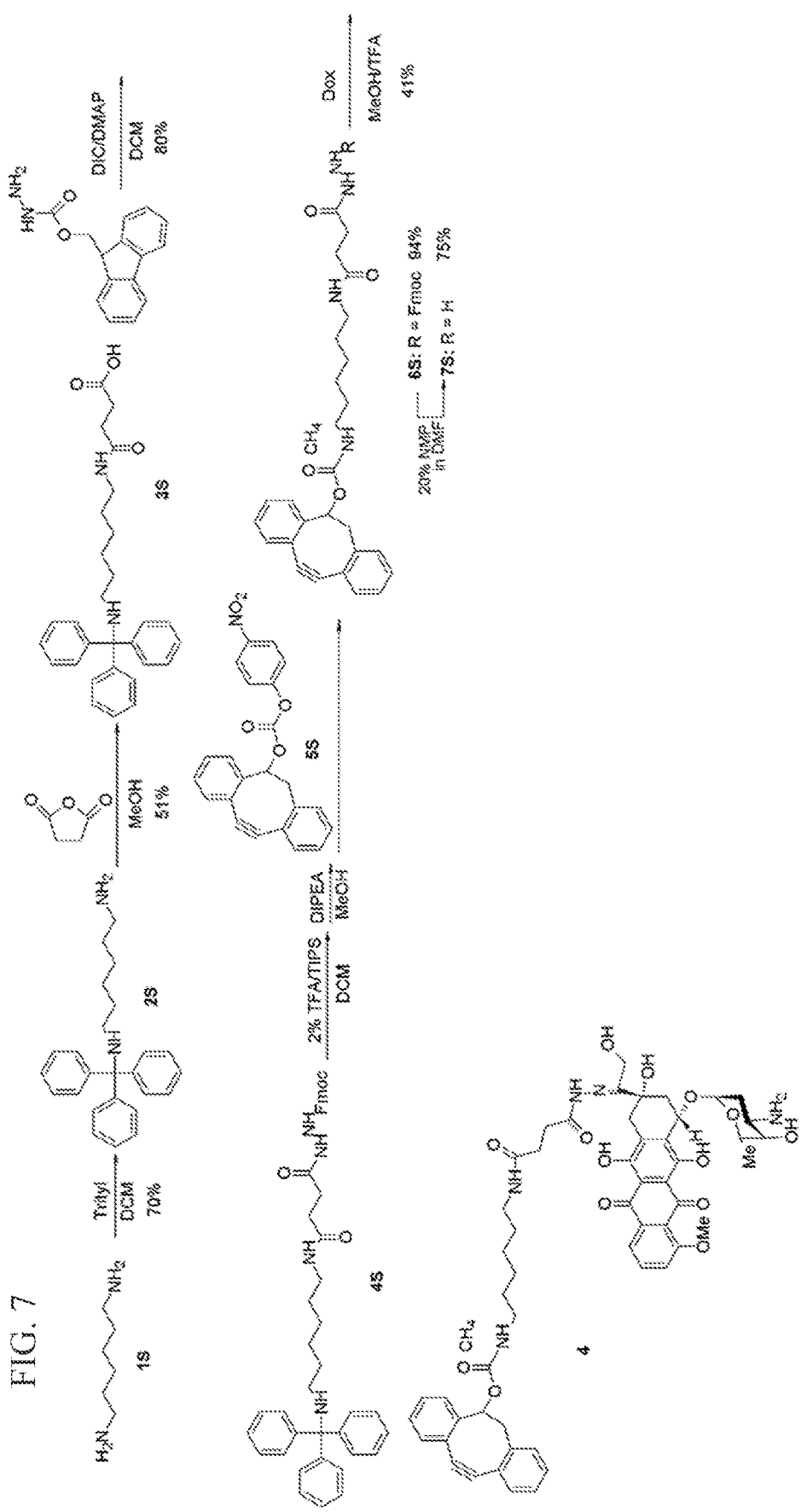
FIG. 7 shows the synthesis of dibenzylcyclooctynol-doxorubicin (DIBO-Dox).
Figure 8:
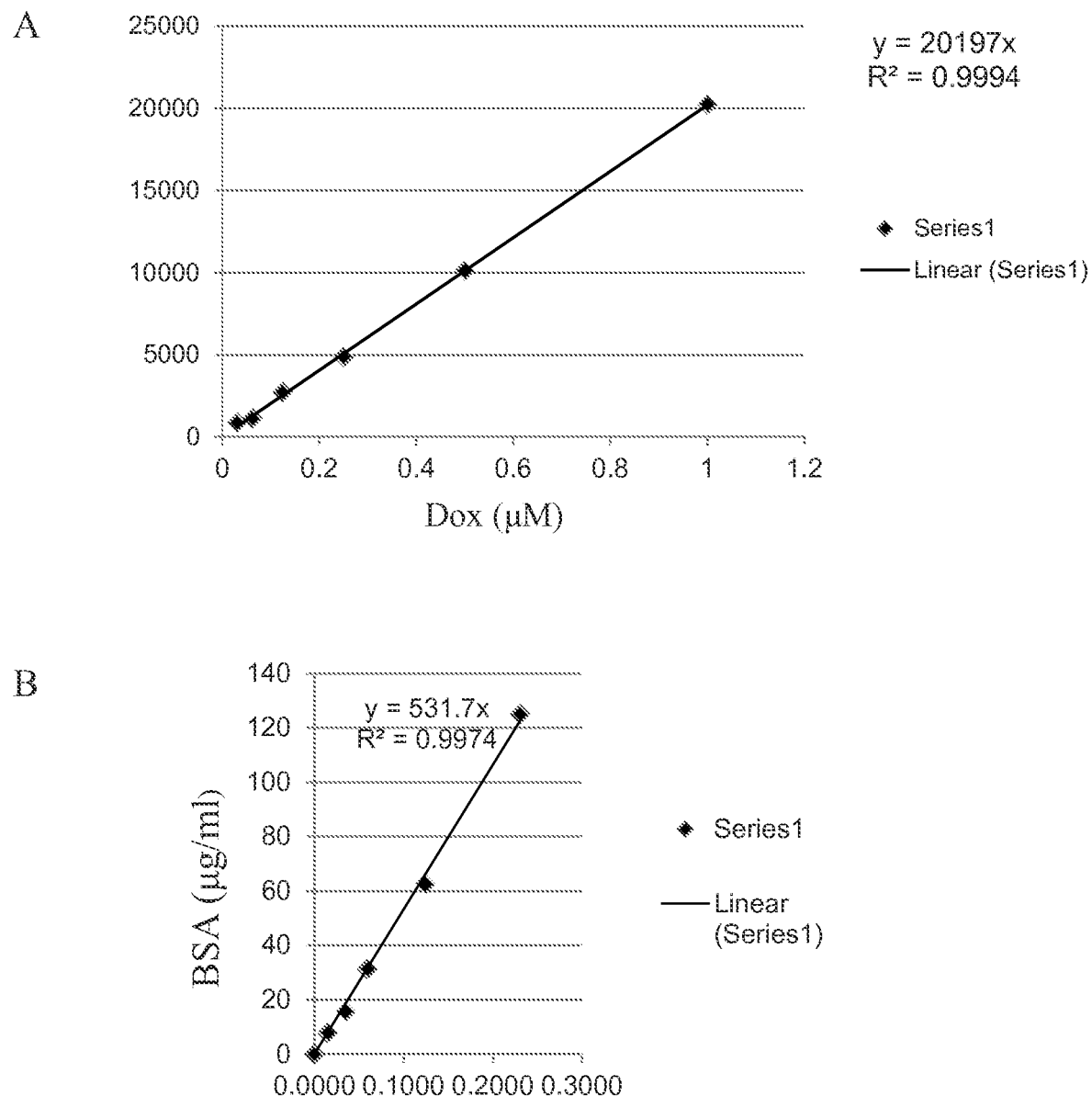
FIG. 8 shows (A) typical standard curve of the fluorescence intensity vs concentration of Dox and (B) concentration of BSA vs UV absorbance for bicinchoninic acid assay (BCA) protein concentration quantification.

Next, compound 4 (FIG. 1), which is composed of DIBO attached to Dox through an acid sensitive hydrazine linker, was synthesized by condensation DIBO modified by a hydrazine linker with the ketone moiety of Dox (FIG. 7). The remodeled control and anti-CD22 antibody were exposed to 4 and analysis of the resulting conjugates by fluorescent intensity measurements (FIG. 8, Table 1) demonstrated the presence of 4.1 and 3.5 Dox molecules per antibody molecule, respectively.

Figure 9:
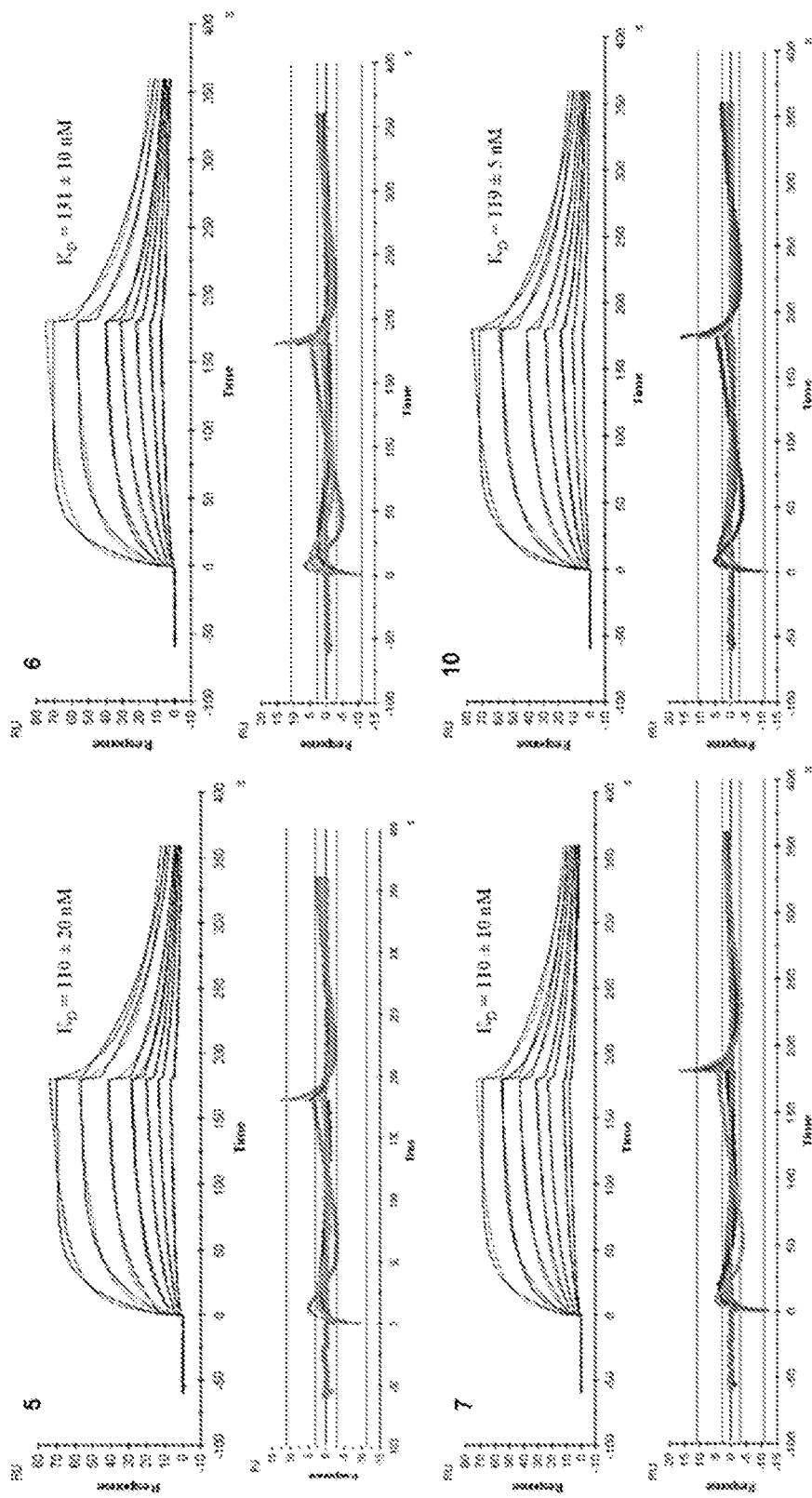
FIG. 9 shows typical surface plasmon resonance (SPR) sensorgrams fitted with a Langmuir 1:1 binding model (black lines) of the binding of IgG and FcγRIIIa receptor and the dissociation constant of the binding ($K_D$). The antibodies were immobilized by protein A capture, and the binding was analyzed by injecting the respective FcγRIIIa receptors at serial two-fold dilutions starting at 0.46 µM.
Figure 10:
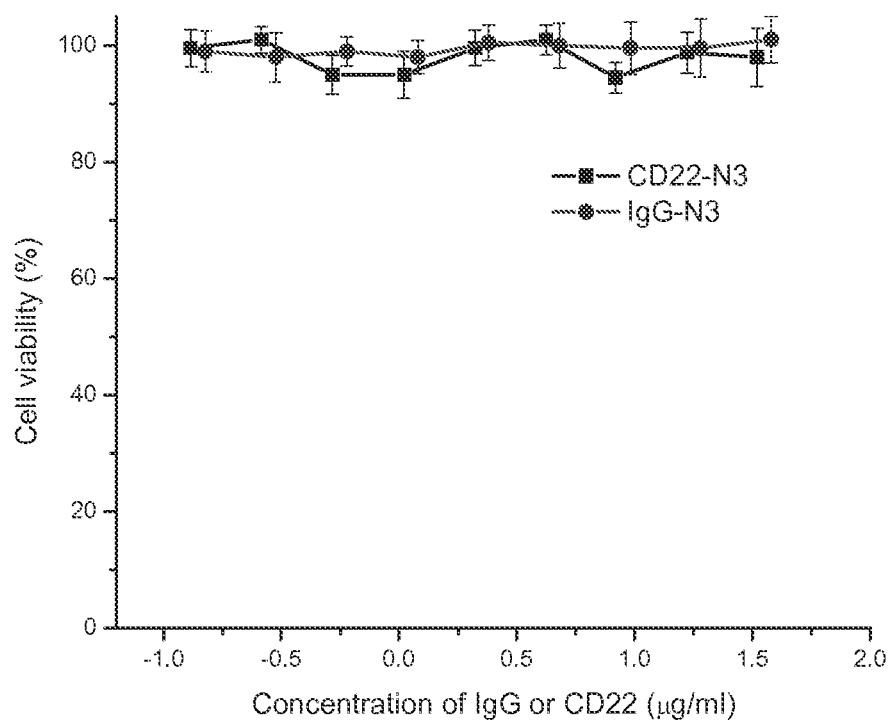
FIGS. 10 and 11 show cytotoxicity results for anti-CD22-Dox.

Although ADC is aimed at delivering cytotoxic drugs selectively to cancer cells, the effector functions of the antibody may also contribute to its anticancer properties.[8] Therefore, the influence of glycan remodeling and attachment of the cytotoxic drug on the binding of Fcγ Receptor IIIA (FcγRIIIa) was analyzed by surface plasmon resonance (SPR).[18] Thus, the various glycoforms of the antibodies were immobilized on a sensor chip modified by protein A and different concentrations of recombinant FcγRIIIa were employed as analyte. The resulting data were fitted to a 1:1 Langmuir binding model to give equilibrium constants ($K_D$) of 110, 131, 110, and 119 nM for the antibodies 5, 6, 7 and 10, respectively (FIG. 9). Surprisingly, these results demonstrate that modification of sialic acid by a C-9 azido moiety and subsequent attachment of a drug does not influence FcγRIIIa binding.

Figure 11:
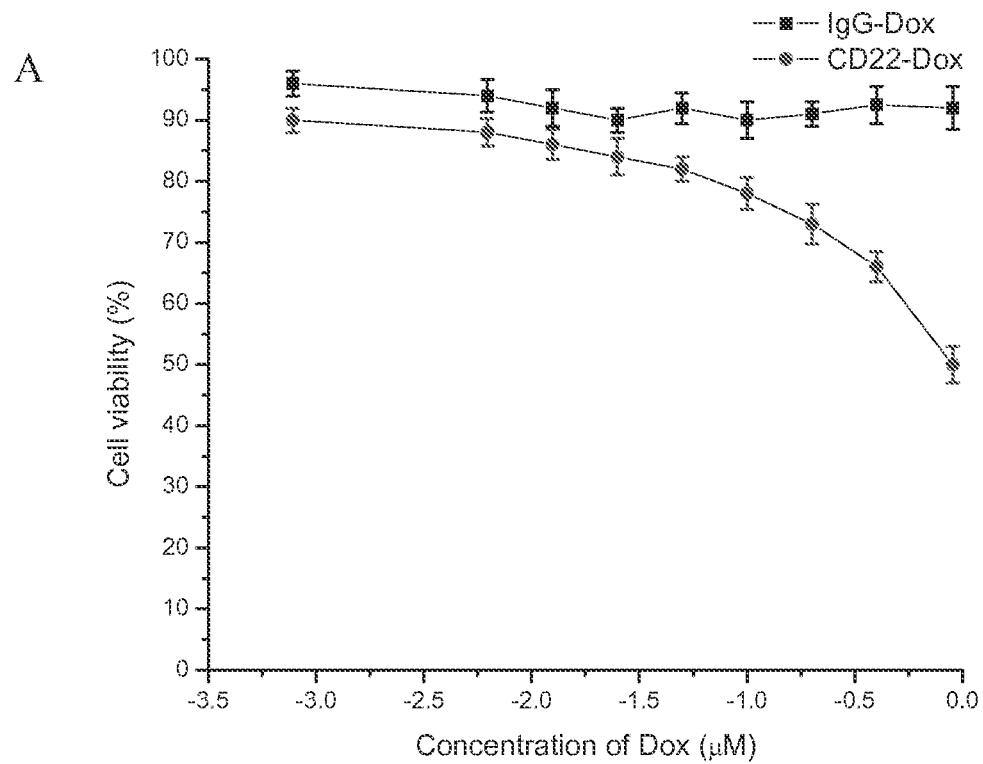
Figure 11:
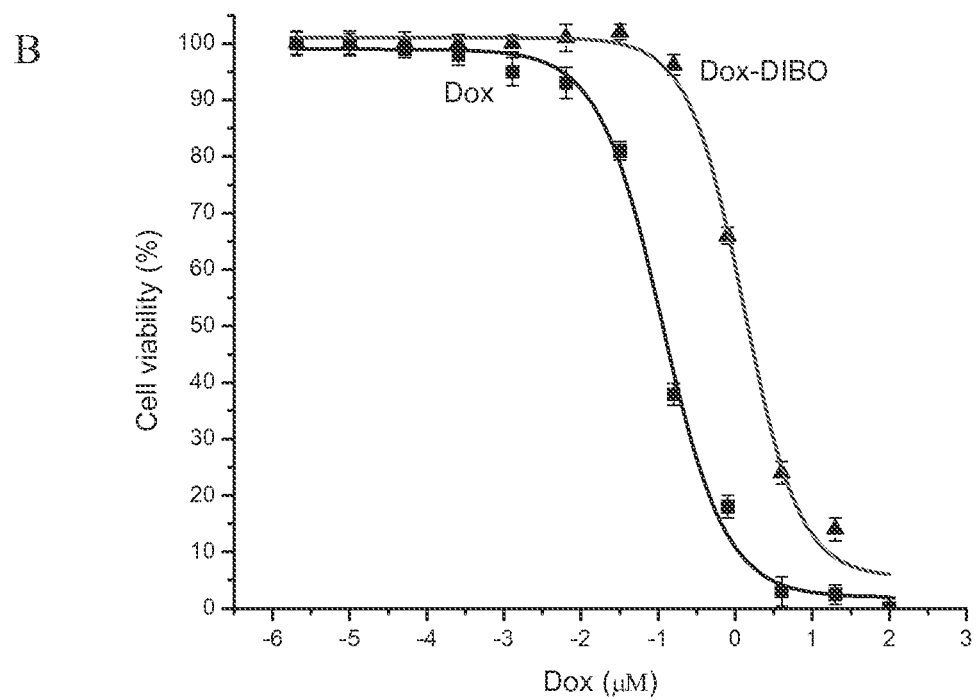
Figure 12:
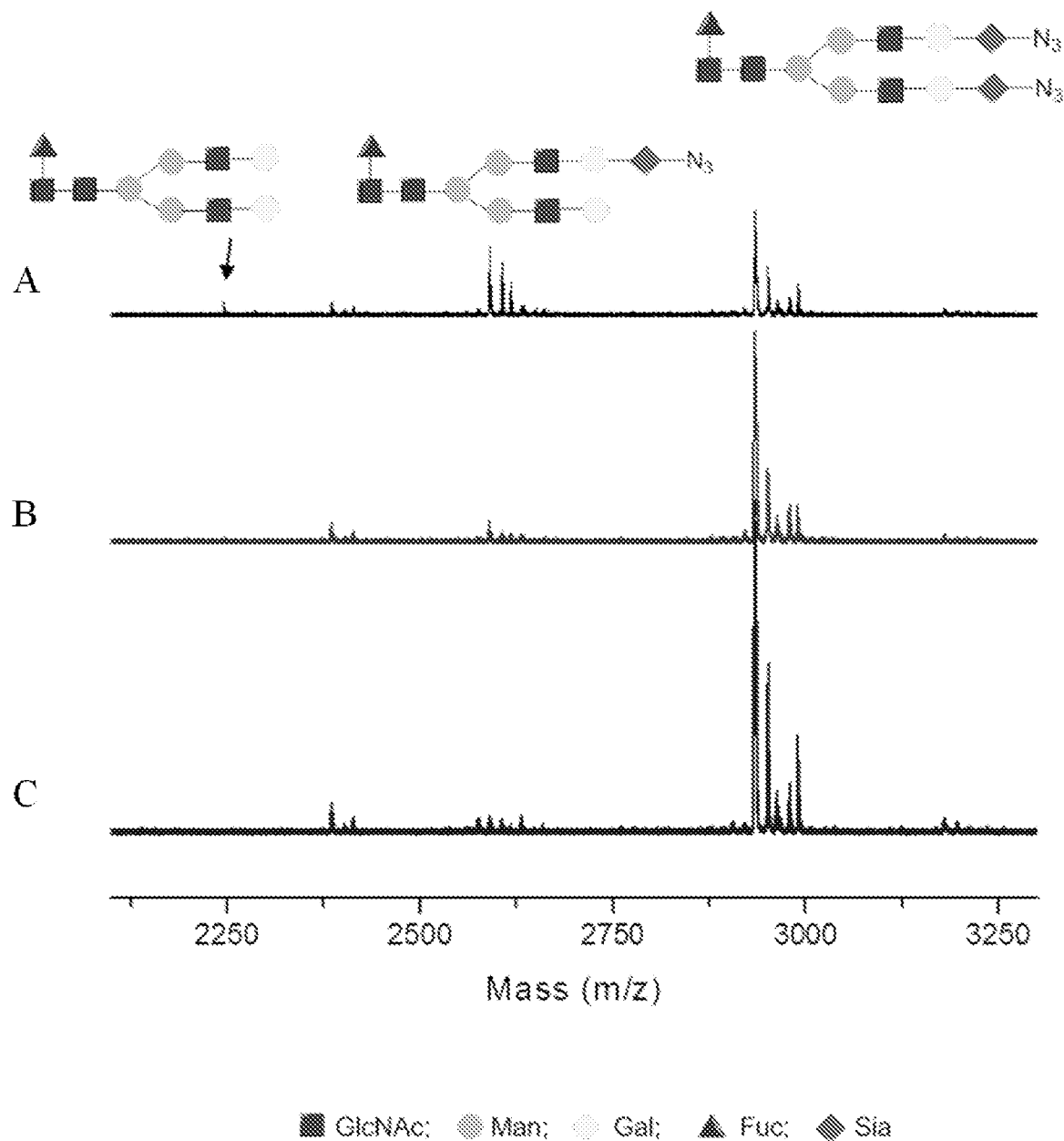
FIG. 12 shows mass spectrometry-based determination of glycan structures of IgG Galactosylation followed by sialylation using ST6Gal I at various reaction times: (A) 24 h, 5-10% of digalactosylated glycan, 30-40% of monosialylated glycan, 60-70% of bisialylated glycan. (B) 72 h, almost no digalactosylated glycan and above 90% of bisialylated glycan. (C) 96 h, almost fully converted to bisialylated glycan.

Next, the cytotoxic properties of the control and anti-CD22 antibodies were examined. The cell surface receptor CD22 is a clinically validated target for B-cell lymphoma that undergoes constitutive endocytosis, and therefore we thought it would be a suitable target for the development of ADCs. Thus, Daudi Burkett lymphoma cells, which express CD22, were incubated with varying concentrations of the anti-CD22 and control antibody with or without Dox modification. After 48 h, cell viability was measured by the activity of the enzymes that reduce tetrazole (MTT) to formazan. As expected, the unmodified antibodies and the control antibody modified by Dox did not exhibit cytotoxicity even at a high concentration of antibody. On the other hand, the anti-CD22 antibody modified by Dox exhibited dose dependent cytotoxicity demonstrating that the antibody is internalized and the drug released for intercalating with DNA. FIG. 11 shows (A) Daudi cells treated with control IgG antibody modified by Dox (squares) and anti-CD22 antibody modified by Dox (circles); (B) Daudi cells treated with anti-CD22 antibody modified by Dox (squares) and Daudi cells treated with anti-CD22 antibody modified by Dox with an acid sensitive hydrazine linker, which in turn is attached to DIBO (triangles.) The influence of modifying Dox with an acid sensitive hydrazine linker, which in turn is attached to DIBO, was also investigated. As can be seen in FIG. 11(B), linkered Dox was only slightly less active than the unmodified drug demonstrating that the hydrazine linkage is cleaved in the acidic environment of endosomes and lysosomes releasing the active drug.

The studies described here demonstrate that ST6Gal 1 is uniquely suited to install azido-containing sialic acids into the glycans of IgG antibodies to give a homogeneous glycoform having approximately four azido functions. We show, for the first time, that a cytotoxic drug can be attached to such an antibody by a strain promoted azide-alkyne cycloaddition. This type of reaction is attractive for bioconjugation because it is highly efficient even in a very complex milieu, does not require a toxic metal catalyst, and proceeds efficiently at ambient temperature. Furthermore, ST6Gal 1 is a very stable protein that can be expressed in large quantities, and it is the expectation that in addition to an azide, it can tolerate other and even more reactive functional groups in its sugar donor such as nitrones (Ning et al., *Angew Chem. Int. Ed.* 2008, 47, 2253-2255; *Angew. Chem.* 2008, 120, 2285-2287), nitrile oxides Sanders et al., *J. Am. Chem. Soc.* 2011, 133, 949-957) or trans-cyclooctene (Selvaraj et al., *Curr. Opin. Chem Biol.* 2013, 17, 753-760). The only other reported method for the site-specific attachment of a drug to the glycan of antibodies involves metabolic labeling with 6-thiofucose.[19] This approach resulted in a relatively low incorporation of drug, depends on a less attractive conjugation approach, and relies on the presence of a core fucose moiety that inhibits many antibody effector functions. Several other methods have been reported to install reactive functional groups in glycans of antibodies. For example, mild periodate oxidation of sialic acids of glycoproteins makes it possible to introduce aldehyde functions, which can then be used for coupling purposes.[20] Such reactions are difficult to control and can lead to oxidation of sensitive amino acids such as methionine. Aldehydes or ketones can also be installed in oligosaccharides of glycoproteins by other means but these methods suffer either from low incorporation of the reactive functionality, the need for complex reagents, less desirable conjugation methods, or the formation of heterogeneous products.[18], [21]

REFERENCES

[1] a) U. Iyer, V. J. Kadambi. *J. Pharmacol. Toxicol. Methods* 2011, 64, 207-212; b) J. R. Adair, P. W. Howard, J. A. Hartley, D. G. Williams, K. A. Chester. *Expert Opin. Biol. Ther.* 2012, 12, 1191-1206.

[2] L. Ducry, B. Stump. *Bioconjug. Chem.* 2010, 21, 5-13.

[3] R. S. Zolot, S. Basu, R. P. Million. *Nat. Rev. Drug Discov.* 2013, 12, 259-260.

[4] J. R. Junutula, H. Raab, S. Clark, S. Bhakta, D. D. Leipold, S. Weir, Y. Chen, M. Simpson, S. P. Tsai, M. S. Dennis, Y. Lu, Y. G. Meng, C. Ng, J. Yang, C. C. Lee, E. Duenas, J. Gorrell, V. Katta, A. Kim, K. McDorman, K. Flagella, R. Venook, S. Ross, S. D. Spencer, W. Lee Wong, H. B. Lowman, R. Vandlen, M. X. Sliwkowski, R. H. Scheller, P. Polakis, W. Mallet. *Nat. Biotechnol.* 2008, 26, 925-932.

[5] a) B. M. Hutchins, S. A. Kazane, K. Staflin, J. S. Forsyth, B. Felding-Habermann, P. G. Schultz, V. V. Smider. *J. Mol. Biol.* 2011, 406, 595-603; b) J. Y. Axup, K. M. Bajjuri, M. Ritland, B. M. Hutchins, C. H. Kim, S. A. Kazane, R. Halder, J. S. Forsyth, A. F. Santidrian, K. Stafin, Y. Lu, H. Tran, A. J. Seller, S. L. Biroc, A. Szydlik, J. K. Pinkstaff, F. Tian, S. C. Sinha, B. Felding-Habermann, V. V. Smider, P. G. Schultz. *Proc. Nat. Acad. Sci. U.S.A* 2012, 109, 16101-16106.

[6] P. Strop, S. H. Liu, M. Dorywalska, K. Delaria, R. G. Dushin, T. T. Tran, W. H. Ho, S. Farias, M. G. Casas, Y. Abdiche, D. Zhou, R. Chandrasekaran, C. Samain, C. Loo, A. Rossi, M. Rickert, S. Krimm, T. Wong, S. M. Chin, J. Yu, J. Dilley, J. Chaparro-Riggers, G. F. Filzen, C. J. O'Donnell, F. Wang, J. S. Myers, J. Pons, D. L. Shelton, A. Rajpal. *Chem. Biol.* 2013, 20, 161-167.

[7] S. Panowski, S. Bhakta, H. Raab, P. Polakis, J. R. Junutula. *mAbs* 2014, 6, 34-45.

[8] R. Jefferis. *Nat. Rev. Drug Discov.* 2009, 8, 226-234.

[9] a) Keppler et al., *Glycobiology* 2001, 11, 11R-18R; b) R. M. Schmaltz, S. R. Hanson, C. H. Wong. *Chem. Rev.* 2011, 111, 4259-4307.

[10] M. F. Debets, C. W. J. van der Doelen, F. P. J. T. Rutjes, F. L. van Delft. *ChemBioChem* 2010, 11, 1168-1184.

[11] a) E. Saxon, C. R. Bertozzi. *Science* 2000, 287, 2007-2010; b) C. I. Schilling, N. Jung, M. Biskup, U. Schepers, S. Brase. *Chem. Soc. Rev.* 2011, 40, 4840-4871.

[12] a) M. Meldal, C. W. Tornoe. *Chem. Rev.* 2008, 108, 2952-3015; b) D. Soriano Del Amo, W. Wang, H. Jiang, C. Besanceney, A. C. Yan, M. Levy, Y. Liu, F. L. Marlow, P. Wu. *J. Am. Chem. Soc.* 2010, 132, 16893-16899; c) D. C. Kennedy, C. S. McKay, M. C. Legault, D. C. Danielson, J. A. Blake, A. F. Pegoraro, A. Stolow, Z. Mester, J. P. Pezacki. *J. Am. Chem. Soc.* 2011, 133, 17993-18001.

[13] a) J. C. Jewett, C. R. Bertozzi. *Chem. Soc. Rev.* 2010, 39, 1272-1279; b) M. F. Debets, S. S. van Berkel, J. Dommerholt, A. T. Dirks, F. P. Rutjes, F. L. van Delft. *Acc. Chem. Res.* 2011, 44, 805-815.

[14] a) Y. Kajihara, T. Kamitani, R. Sato, N. Kamei, T. Miyazaki, R. Okamoto, T. Sakakibara, T. Tsuji, T. Yamamoto. *Carbohydr. Res.* 2007, 342, 1680-1688; b) N. E. Mbua, X. Li, H. R. Flanagan-Steet, L. Meng, K. Aoki, K. W. Moremen, M. A. Wolfert, R. Steet, G. J. Boons. *Angew. Chem. Int. Ed.* 2013, 52, 13012-13015; *Angew. Chem.* 2013, 125, 13250-13253.

[15] X. H. Ning, J. Guo, M. A. Wolfert, G. J. Boons. *Angew. Chem., Int. Ed.* 2008, 47, 2253-2255; *Angew. Chem.* 2008, 120, 2285-2287.

[16] A. W. Barb, L. Meng, Z. Gao, R. W. Johnson, K. W. Moremen, J. H. Prestegard. *Biochemistry* 2012, 51, 4618-4626.

[17] H. Yu, H. Chokhawala, R. Karpel, H. Yu, B. Wu, J. Zhang, Y. Zhang, Q. Jia, X. Chen. *J. Am. Chem. Soc.* 2005, 127, 17618-17619.

[18] W. Huang, J. Giddens, S. Q. Fan, C. Toonstra, L. X. Wang. *J. Am. Chem. Soc.* 2012, 134, 12308-12318.

[19] N. M. Okeley, B. E. Toki, X. Zhang, S. C. Jeffrey, P. J. Burke, S. C. Alley, P. D. Senter. *Bioconjug. Chem.* 2013, 24, 1650-1655.

[20] a) J. D. Rodwell, V. L. Alvarez, C. Lee, A. D. Lopes, J. W. Goers, H. D. King, H. J. Powsner, T. J. McKearn. *Proc. Natl. Acad. Sci. U.S.A.* 1986, 83, 2632-2636; b) L. Van Lenten, G. Ashwell. *J. Biol. Chem.* 1971, 246, 1889-1894; Zuberbuhler et al., *Chem. Commun.* 2012, 48, 7100-7102.

[21] a) A. G. Morell, C. J. Van den Hamer, I. H. Scheinberg, G. Ashwell. *J. Biol. Chem.* 1966, 241, 3745-3749; b) E. Boeggeman, B. Ramakrishnan, M. Pasek, M. Manzoni, A. Puri, K. H. Loomis, T. J. Waybright, P. K. Qasba. *Bioconjug. Chem.* 2009, 20, 1228-1236.

Supporting Information

General Methods and Materials

NeuAc was purchased from Carbosynth LLC. Other reagents were obtained from commercial sources and used as purchased. Dichloromethane (DCM) was freshly distilled using standard procedures. Other organic solvents were purchased anhydrous and used without further purification.

Unless otherwise noted, all reactions were carried out at RT in oven-dried glassware with magnetic stirring. Organic solutions were concentrated under diminished pressure with bath temperatures <40° C. Flash column chromatography was carried out on silica gel G60 (Silicycle, 60-200 μm, 60 Å). Thin-layer chromatography (TLC) was carried out on Silica gel 60 $F_{254}$ (EMD Chemicals Inc.) with detection by UV absorption (254 nm) where applicable, by spraying with 20% sulfuric acid in ethanol followed by charring at 150° C. or by spraying with a solution of $(NH_4)_6Mo_7O_{24} \cdot H_2O$ (25 g/L) in 10% sulfuric acid in ethanol followed by charring at –150° C. $^1H$ and $^{13}C$ NMR spectra were recorded on a Varian Inova-300 (300/75 MHz), a Varian Inova-500 (500 MHz) and a Varian Inova-600 (600/150 MHz) spectrometer equipped with sun workstations. Multiplicities are quoted as singlet (s), doublet (d), doublet of doublets (dd), triplet (t) or multiplet (m). All NMR signals were assigned on the basis of $^1H$ NMR, $^{13}C$ NMR, gCOSY and gHSQC experiments. All chemical shifts are quoted on the δ-scale in parts per million (ppm). Signals marked with a superscript Roman numeral I were the reducing end, whereas II and III were the second and the third sugar from the reducing end. Residual solvent signals were used as an internal reference. Mass spectra were recorded on an Applied Biosystems 5800 MALDI-TOF or Shimadzu LCMS-IT-TOF mass spectrometer. The matrix used was 2,5-dihydroxy-benzoic acid (DHB). Reverse-Phase HPLC was performed on an Aglient 1200 series system equipped with an autosampler, fraction-collector, UV-detector and eclipse XDB-C18 column (5 μm, 4.6×250 mm or 9.4×250 mm). Fluorescent spectroscopy was carried on a BMG Labtech POLAR star optima.

N-Linked Glycans Analysis of IgG and Anti-CD22

Chemicals and Enzymes: Peptide N-glycosidase F was purchased from New England BioLabs. Trypsin, I-2,3-Sialidase (Jack beans) and L-N-acetylhexosaminidase (Jack beans) were obtained from Sigma. Other fine chemicals were from standard sources.

Release of N-linked glycans: An aliquot of the sample was dried in a Speed Vac (Savant SC 110) and re-dissolved in ammonium bicarbonate buffer (50 mM, pH 8.4) and heated at 100° C. for 5 min to denature the glycoprotein prior to trypsin digestion (37° C., overnight) and purified by passing through a C18 reversed phase cartridge to give a glycopeptides followed by adding a second enzyme, peptide N-glycosidase F (PNGase F, New England BioLabs) and incubated at 37° C. overnight to release the N-linked glycans. After enzymatic digestions, the sample was passed through a C18 reversed phase cartridge. The carbohydrate fraction was eluted with 5% acetic acid and then was dried by lyophilization.

Glycan analysis by matrix-assisted laser-desorption ionization time-of-flight mass spectrometry (MALDI/TOF-MS) and ESI: The released N-glycans were permethylated with NaOH and methyl iodide using the procedure of Anamula et al. (Anumula et al., Anal Biochem 1992, 203:101-108). Permethylated glycans were analyzed using ESI (Shimadzu LCMS-IT-TOF mass spectrometer) directly or crystallized on a MALDI plate with 2, 3-dihydroxybenzoic acid (DHBA, 20 mg/mL solution in 50% methanol:water) as a matrix and analyzed using MALDI/TOF-MS (5800 Proteomics analyzer, Applied Biosystems). All spectra were acquired in the reflector positive ion mode.

Remodeling of the IgG or Anti-CD22 N-Glycans

Materials: All chemicals were obtained from Sigma, unless otherwise noted. Cytidine-5'-(5-acetamido-9-azido-3,5,9-tri-deoxy-β-D-glycero-D-galacto-2-nonulopyranosylonic acid monophosphate) (CMP-Neu5Ac9N3) and recombinant rat α-(2,6)-sialyltransferase (GFP-ST6Gal I) were prepared according to the previous report (Mbua et al., Angewandte Chemie, 2013, 52(49):13012-13015).

Procedure: Pure immunoglobulin G (IgG) (Athens Research and Technology, Athens GA) was dialyzed overnight against water and lyophilized. Galactosylation of the N-glycan was achieved by resuspending the resulting material in 50 mM MOPS, 20 mM $MnCl_2$, 10 mM UDP-galactose, pH 7.2, 80 g/ml BSA, 85 U/ml calf intestine alkaline phosphatase, to a concentration of 30 mg/ml IgG. This was followed by addition of 100 mU/mL bovine β-1,4-galactosyl transferase and incubation at 37° C. for 24 h. To ensure complete galactosylation, an additional aliquot of UDP-galactose and galactosyl transferase were added to the reaction and incubated at 37° C. for an additional 24 h. The galactosylated IgG was purified using a Protein A Sepharose Column (GE Healthcare) and the solution was exchanged in 50 mM cacodylate, pH 7.6 using an Amicon 10 kDa cutoff spin concentrator (Millipore). A reaction was conducted with a final concentration of 50 mM cacodylate, 4 mM CMP-Neu5Ac9N3, 14 mg/ml IgG, 80 μg/ml BSA, 85 U/ml calf intestine alkaline phosphatase and 1.5 mg/ml GFP-ST6Gal I at pH 7.6 and incubated at 37° C. for 96 h followed by Protein A Sepharose Column purification and buffer exchanging to 50 mM cacodylate. The extent of sialylation was monitored by MALDI-MS as described previously using an Applied Biosystems SCIEX TOF/TOF 5800 mass spectrometer. Following every 24 h incubation, the sample was buffer exchanged with 50 mM cacodylate, pH7.6 using an Amicon 10 kDa cutoff spin concentrator to remove CMP, an inhibitor of ST6Gal I and an additional aliquots of CMP-Neu5Ac9N3 and α2-6 sialyltransferase were added back to this washed preparation. This incubation/buffer exchange process was repeated twice, followed by a final fourth 24 h incubation at 37° C., and resulted in a highly disialylated IgG preparation (>95%). The anti-CD22 was remodeled employing the same procedure with IgG.

Analysis of Neu5Ac and Neu5Ac9N3 of the IgG and Remodeling IgG

Sialic acid analysis was conducted by High-pH anion-exchange chromatography (HPAEC) using an ICS-3000 Ion Chromatography System (Dionex, Sunnyvale, CA, USA) with 100 mM NaOH and 1 M sodium acetate in 100 mM NaOH. The system consists of a SP gradient pump with an AS autosampler, ICS-3000 thermal compartment, and an ICS-3000 electrochemical detector equipped with an amperometry cell. The cell consists of a gold electrode, a combination reference electrode of glass and Ag/AgCl (3 M KCl) and titanium counter electrode consisting of the cell body. Separation was carried out using the CarboPac PA 20 column set consisting of an amino trap column (30 mm×3 mm I.D.) and an analytic column (150 mm×3 mm I.D.) The column and the electrochemical detection cell were placed inside the ICS-3000 thermal compartment for temperature control. The chromatographic system control, data acquisition and analysis were carried out using Chromeleon Software (Dionex). Sample preparation: 0.2-0.8 mg of IgG and remodeled IgG and two sugars standard, Neu5Ac and Neu5Ac9N3 were treated with 2 M acetic acid in water (400 μL) at 80° C. for 3 h. Sample and standard were dried by spin-vacuo centrifugation, redissolved in quantitative volume of water. The content of Neu5Ac and Neu5Ac9N3 in the sample was determined based on the calibration curves of the corresponding standards.

The Synthesis of DIBO-FITC

See, e.g., Ning et al., *Angew. Chem. Int. Ed. Engl.* 2008, 47, 2253-2255.

The synthesis of DIBO-Doxorubicin 4-oxo-4-((6-(tritylamino)hexyl)amino)butanoic acid (3S). In separated vials, succinic anhydride (300 mg, 3 mmol) and trityl amine 2S (Zou et al., *Carbohydr. Res.* 2008, 343:2932-8) (1.4 g, 4.3 mmol) were dissolved in EtOH. After cooling the succinic anhydride/EtOH solution to 0° C., 2S in EtOH (8 M) was added drop wise at this temperature then the ice bath was removed. The reaction mixture was stirred at room temperature until succinic anhydride was fully dissolved. The solvent was removed in vacuo. The residue was purified by silica gel column chromatography (DCM/MeOH, 12/1 →8/1, v/v) to give 3S (700 mg, 51%). $R_f$=0.15 (DCM/MeOH, 12/1); $^1$H NMR (600 MHz, CDCl$_3$) δ 7.55-7.01 (m, 15H, ArH), 3.11 (dd, J=12.8, 6.8 Hz, 2H, $CH_2^I$), 2.56 (t, J=6.7 Hz, 2H, $CH_2^{II}$), 2.40 (t, J=6.7 Hz, 2H, $CH_2^{II}$), 2.24 (t, J=7.3 Hz, 2H, $CH_2^I$), 1.57-1.43 (m, 2H, $CH_2^I$), 1.42-1.27 (m, 2H, $CH_2^I$), 1.27-1.05 (m, 4H, 2×$CH_2^I$); $^{13}$C NMR (150 MHz, CDCl$_3$): δ 176.53, 172.96, 144.49, 128.71, 128.64, 127.99, 127.94, 127.80, 126.76, 72.03, 44.14, 39.43, 31.54, 30.97, 29.48, 29.03, 26.70, 26.54; HR MALDI-TOF MS: m/z: calcd for $C_{29}H_{34}N_2O_3Na$ [M+Na]+: 481.2467; found: 481.2444.

Fluorenylmethyloxy 2-(4-oxo-4-((6-(tritylamino)hexyl)amino)butanoyl)hydrazinecarboxylate (4S). In a 10 ml round bottom flask, 3S (100 mg, 0.23 mmol) was dissolved in DCM (2 ml), DMF (0.5 ml) followed by the addition of 9-fluorenylmethyl carbazate (50 mg, 0.20 mmol), DIC (36 μL, 0.23 mmol) and catalytic DMAP. After stirring at room temperature for 16 h, the reaction mixture was loaded directly onto LH-20 column (DCM/MeOH, 1/1, v/v) to give 4S (110 mg, 80%). $R_f$=0.21 (DCM/MeOH, 12/1); $^1$H NMR (600 MHz, CD$_3$OD) δ 7.90-7.01 (m, 23H, ArH), 4.36 (d, J=7.1 Hz, 2H, $CH_2^{Fmoc}$), 4.22 (t, 1H, J=7.0 Hz, $CH^{Fmoc}$), 3.10 (t, J=7.2 Hz, 2H, $CH_2$), 2.55-2.38 (m, 4H, 2×$CH_2$), 2.08 (t, J=7.2 Hz, 2H, $CH_2$), 1.57-1.35 (m, 4H, 2×$CH_2$), 1.23 (br s, 4H, 2×$CH_2$); $^{13}$C NMR (selected HSQCAD, 150 MHz, CD$_3$OD): δ 130.45-115.70 (Ar), 67.00 ($CH_2^{Fmoc}$) 48.58 ($CH_2$), 46.57 ($CH^{Fmoc}$) 43.29 ($CH_2$), 38.81 ($CH_2$), 29.69 ($CH_2$), 28.56 ($CH_2$), 27.81 ($CH_2$), 26.51 ($CH_2$), 26.31 ($CH_2$); HR MALDI-TOF MS: m/z: calcd for $C_{44}H_{46}N_4O_4Na$ [M+Na]+: 717.3417; found: 717.3395.

DIBO hydrazide derivative (6S). A mixture of solution 1.5 ml (2% TFA, 2% TIPS in DCM, v/v) was added to 4S (20 mg) in a 5 ml conical vial. The reaction mixture was stirred at room temperature for 30 min until TLC showed the disappearance of starting material. The reaction was quenched by the addition of DIPEA (500 μL), then MeOH (1.5 ml), 5S (Ning et al., Agnew Chem. Int. Ed. Engl. 2008, 47(12):2253-5) (20 mg) were added. The mixture was stirred for 16 h at room temperature. The solution was concentrated by blowing air. The residue was purified by silica gel column chromatography (Tol/Acetone, 2/1, v/v) to give 6S (19 mg, 94%). $R_f$=0.28 (Tol/Acetone, 1/1); $^1$H NMR (600 MHz, CD$_3$OD) δ 7.98-6.88 (m, 16H, ArH), 5.40 (s, 1H, $CH^{DIBO}$), 4.36 (d, J=7.1 Hz, 2H, $CH_2^{Fmoc}$), 4.22 (t, J=7.1 Hz, 1H, $CH^{Fmoc}$), 3.22-2.95 (m, 5H, 2×$CH_2$, $CHH^{DIBO}$), 2.79 (dd, J=15.0, 3.7 Hz, 1H, $CHH^{DIBO}$), 2.61-2.35 (m, 4H, 2×$CH_2$), 1.68-1.17 (m, 8H, 4×$CH_2$); $^{13}$C NMR (150 MHz, CD$_3$OD): δ 156.58, 152.30, 151.01, 143.64, 141.13, 129.55, 128.50, 128.48, 127.88, 127.77, 127.71, 127.39, 126.86, 126.80, 126.76, 125.72, 125.45, 124.87, 124.83, 124.66, 123.54, 123.47, 120.99, 119.50, 112.37, 109.55, 78.39, 76.37, 67.21, 46.78, 45.75, 40.23, 38.91, 30.36, 29.34, 28.84, 28.68, 26.10, 25.97; HR ESI-TOF MS: m/z: calcd for $C_{42}H_{42}N_4O_6Na$ [M+Na]+: 721.3002; found: 721.3011.

DIBO hydrazide derivative (7S). 4-methylpiperidine in DMF (300 μL, 20% v/v) was added to 6S (6 mg) in a 5 ml conical vial. The reaction mixture was stirred at room temperature for 30 min until TLC showed the disappearance of starting material. The reaction mixture was directly loaded onto LH-20 (MeOH/DCM, 1/1, v/v) and purified to give 7S (3 mg, 75%). $R_f$=0.18 (Tol/Acetone, 1/1); $^1$H NMR (600 MHz, CD$_3$OD) δ 7.58-7.08 (m, 8H, ArH), 5.32 (s, 1H, $CH^{DIBO}$), 3.11 (dd, J=15.1, 2.2 Hz, 1H, $CHH^{DIBO}$), 3.12-2.92 (m, 4H, 2×$CH_2$), 2.72 (dd, J=15.0, 3.9 Hz, 1H, $CHH^{DIBO}$), 2.40-2.15 (m, 4H, 2×$CH_2$), 1.53-1.12 (m, 8H, 4×$CH_2$); $^{13}$C NMR (150 MHz, CD$_3$OD): δ 172.84, 172.57, 156.59, 152.32, 151.02, 129.56, 127.89, 127.78, 126.87, 126.82, 125.73, 125.46, 123.55, 123.46, 120.99, 112.37, 109.55, 76.38, 52.11, 45.75, 40.22, 38.85, 30.64, 29.35, 28.92, 28.85, 26.08, 25.96, 6.15; HR ESI-TOF MS: m/z: calcd for $C_{27}H_{32}N_4O_4Na$ [M+Na]+: 499.2322; found: 499.2306.

DIBO-Doxorubicin conjugate (4). 7S (17 mg, 0.036 mmol) and doxorubicin·HCl (17 mg, 0.029 mmol) were dissolved in anhydrous MeOH (2 ml) followed by the addition of TFA (15 μL), the reaction mixture was stirred at room temperature for 48 h and kept protected from light. The reaction mixture was loaded directly to LH-20 column. Fractions with red color were checked by TLC again, unreacted 7S was recovered. Fractions at bigger molecular weight range corresponding to product were collected to give 4 (12 mg, 41%). $^1$H NMR (600 MHz, CD$_3$OD) δ 8.07-6.96 (m, 12H, ArH), 5.36 (s, 1H, H-$1^{Doxo\text{-}sugar}$), 5.24 (s, 1H, $CH^{DIBO}$), 4.95 (s, 1H, $CH^{Doxo\text{-}\alpha\text{-}carbonyl}$), 4.61-4.35 (m, 2H), 4.24-4.03 (m, 1H, CH), 3.97-3.76 (m, 1H, CH), 3.54 (s, 1H, CH), 3.48-3.37 (m, 1H), 3.30-3.20 (m, 1H, CH), 3.12-2.92 (m, 5H, $CHH^{DIBO}$, 2×$CH_2$), 2.84 (d, J=17.8 Hz, 1H, CHH), 2.78-2.56 (m, 2H, CH2, $CH^{DIBO}$), 2.48 (dd, J=26.2, 6.0 Hz, 1H, CHH), 2.41-2.13 (m, 3H, $CH_2$, CHH), 1.99-1.87 (m, 2H, $CH_2$), 1.87-1.71 (m, 2H, $CH_2$), 1.52-1.07 (m, 11H, 4×$CH_2$, $CH_3^{Doxo}$); $^{13}$C NMR (150 MHz, CD$_3$OD): δ 186.94, 186.51, 175.01, 172.94, 161.03, 156.55, 156.38, 154.57, 153.51, 152.21, 150.98, 135.73, 135.63, 135.16, 134.84, 129.55, 127.85, 127.75, 126.81, 126.75, 125.69, 125.41, 123.45, 120.89, 120.33, 119.10, 118.76, 112.32, 111.06, 110.86, 109.49, 99.56, 76.30, 72.69, 66.60, 66.48, 57.40, 55.65, 45.74, 40.14, 38.77, 33.40, 29.50, 29.34, 28.86, 28.05, 27.35, 26.00, 25.86, 15.66; HR ESI-TOF MS: m/z: calcd for $C_{54}H_{60}N_5O_{14}$ [M+H]+: 1002.4137; found: 1002.4106.

The Conjugation and Quantification of Azido-Labeled IgG and Anti-CD22 with DIBO-FITC or DIBO-Biotin or DIBO-Doxorubicin DIBO-FITC, Biotin or Dororubicin (final con: 45 M) was added to the remodeled IgG or anti-CD22 (final con: 0.4 mg/ml) in cacodylate buffer, pH 7.6. The mixture was placed in a shaker for 2 h at room temperature and the excess of click reagent was removed by washing with cacodylate buffer or PBS buffer in a 10 KDa cutoff spin filer (Millipore). The conjugates of IgG or anti-CD22 with the corresponding click moiety were taken up to desire volume in cacodylate buffer or PBS buffer for MTT assay. The fluorescence intensity of the dilution of the conjugates together with the series of standards was measured using a microplate reader (BMG Labtech) and the concentration of protein was quantified by using the bicinchoninic acid assay (BCA, Pierce Biotechnology). The fluorescence intensity was expressed as fluorescence (AU) per μg total protein.

Qualification of Azido-Labeled IgG by Gel Electrophoresis

Detection of FITC: The native samples (20 μg of protein) were resolved on 4-15% SDS-PAGE gels (Bio-Rad). The gel was imaged using Typhoon 9410 Variable mode imager (Amersham Biosciences) for detection of glycoprotein band with fluorescence followed by Coomassie stain (Thermo Fisher Gelcode blue stain reagent) to show the protein loading.

Detection of Biotin: The denatured samples (20 μg of protein) were resolved on two 4-15% SDS-PAGE gels with equal amount of IgG and the same pattern. One of the gels was stained with Thermo Fisher Gelcode blue stain reagent to confirm the protein loading and the protein in the other gel were and transferred to a nitrocellulose membrane. Next, the membrane was blocked in blocking buffer (nonfat dry milk (5%, Bio-Rad) in PBST (PBS containing 0.1% Tween-20 and 0.1% Triton X-100) for 2 h at RT. The blocked membrane was incubated for 1 h at RT with an anti-biotin antibody conjugated to HRP (1:100,000, Jackson ImmunoResearch Laboratories) in blocking buffer and washed with PBST (4×10 min). Final detection of HRP activity was performed using ECL Plus chemiluminescent substrate (Amersham), exposure to film (Kodak) and development using a digital X-ray imaging machine (Kodak).

Surface Plasmon Resonance (SPR) Binding Experiments.

The binding interaction between different glycoforms of IgG and FcγRIIIa receptors was examined by surface plasmon resonance (SPR) using a Biacore T100 instrument (Biacore Inc., GE Healthcare, USA). Protein A was immobilized by standard amine coupling using an amine coupling kit (Biacore Inc., GE Healthcare). The surface was activated using freshly mixed N-hydroxysuccimide (NHS; 100 mM) and 1-(3-dimethylaminopropyl)-ethylcarbodiimide (EDC; 391 mM) (1/1, v/v) in water. Next, Protein A (200 μg/mL) in aqueous NaOAc (10 mM, pH 4.5) was passed over the chip surface until a ligand density of approximately 5000 RU was achieved. The remaining active esters were quenched by aqueous ethanolamine (1.0 M; pH 8.5). The control flow cell was activated with NHS and EDC followed by immediate quenching with ethanolamine. HBS-EP (0.01 M HEPES, 150 mM NaCl, 3 mM EDTA, 0.005% polysorbate 20; pH 7.4) and HBS-P (0.01 M HEPES, 150 mM NaCl, 0.05% v/v surfactant P20; pH 7.4) were used as the running buffer for the immobilization. Each individual glycoform of IgG in HBS-P buffer (10 mM HEPES pH 7.4, 0.15 M NaCl, 0.05% v/v surfactant P20) was injected at 10 L/min onto the protein A surface and reached the capture level of 150 RU. A serial dilution of FcγIIIa receptors in HBS-P buffer and a 30 μL/min of flow rate were employed for association and dissociation at a constant temperature of 25° C. After each cycle, the surface was regenerated and achieved prior baseline status by injecting 10 mM glycin-HCl, pH 2.0 at 10 L/min for 30 s. Data were fitted into a 1:1 Langmuir binding model using BIAcore T100 evaluation software to obtain the equilibrium constant ($K_D$) data.

Cell Lines and Culture

Human B lymphoblast cell, Daudi (CCL-213, ATCC) were cultured in ATCC-formulated RPMI-1640 medium with L-glutamine (2 mM), sodium bicarbonate (1.5 g $L^{-1}$), glucose (4.5 g $L^{-1}$), HEPES (10 mM) and sodium pyruvate (1.0 mM). The media was supplemented with penicillin (100 ug m$L^{-1}$)/streptomycin (100 μg m$L^{-1}$, Mediatech) and fetal bovine serum (FBS, 10%, BenchMark). Cells were maintained in a humid 5% $CO_2$ atmosphere at 37° C. and subcultured every 2-3 days.

Cytotoxicity Assay in Daudi Cells

Cytotoxicity of CD22-DOX treatments in Daudi cells was determined by use of the mTT uptake assay. On the day of the exposure assay, exponentially growing cells were plated as 50000 cells/well in 180 μL in 96-well tissue culture plates (Nunc). Cells were then incubated with fresh medium (control), IgG, CD22, IgG-DOX, CD22-DOX, DOX or DIBO-DOX (20 μL, 10× in cell culture medium from PBS buffer) for 48 h to give a final volume of 200 μL/well. The viability was measured by quantifying the cellular ability to reduce the water soluble tetrazolium dye 3-4,5-dimethylthiazole-2, 5-diphenyl tetrazolium bromide (MTT) to its insoluble formazan salt as follows. At 44 h, MTT (5 mg mL-1 in PBS, 10 μL/well) was added to the wells and the cells were further incubated for 4 h. At 48 h the supernatant was carefully removed and the water-insoluble formazan salt was dissolved in DMSO (120 μL/well). The absorbance was measured at 560 nm using a microplate reader (BMG Labtech). Data points were collected in triplicate and expressed as normalized values for untreated control cells (100%).

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The complete disclosures of all patents, patent applications including provisional patent applications, publications including patent publications and nonpatent publications, and electronically available material (including, for example, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of making an antibody-drug conjugate, comprising the step of conducting a cycloaddition reaction between:
   a) an antibody comprising an N-linked oligosaccharide comprising at least one functionalized terminal sialoside; and
   b) a functionalized cytotoxic drug molecule,
   wherein one of the functionalized terminal sialoside or functionalized cytotoxic drug molecule comprises a 1,3 dipole or 1,2,4,5 tetrazine, and the other comprises a cyclooctyne or trans cyclooctene, wherein the N-linked oligosaccharide comprising at least one functionalized terminal sialoside is prepared by glycosylating an antibody comprising an N-linked oligosaccharide comprising at least one terminal galactose with a functionalized CMP-sialic acid donor in the presence of a sialyl transferase, and wherein the N-linked oligosaccharide comprises a biantennary glycan, both arms of the biantennary glycan comprise a terminal galactose, and both arms are glycosylated with a functionalized CMP-sialic acid donor in the presence of a sialyl transferase.

2. The method according to claim 1, wherein the antibody comprises 1, 2, 3 or 4 terminal sialosides.

3. The method according to claim 1, wherein the antibody is of the IgG class.

4. The method according to claim 1, wherein the N-linked oligosaccharide is glycosylated to the antibody through an asparagine residue.

5. The method according to claim 4, wherein the N-linked oligosaccharide is glycosylated to the antibody at Asn297.

6. The method according to claim 1, wherein the functionalized terminal sialoside comprises a 1,3 dipole or 1,2,4,5 tetrazine, and the functionalized cytotoxic drug molecule comprises a cyclooctyne or trans cyclooctene.

7. The method according to claim 1, wherein the functionalized cytotoxic drug molecule comprises a linker between the cytotoxic drug molecule and the cyclooctyne or trans cyclooctene.

8. The method according to claim 7, wherein the linker is a cleavable linker.

9. The method according to claim 1, wherein the functionalized terminal sialoside comprises a cyclooctyne or trans cyclooctene, and the functionalized cytotoxic drug molecule comprises a 1,3 dipole or 1,2,4,5 tetrazine.

10. The method according to claim 1, wherein the 1,3 dipole is selected from azide, nitrone, nitrile oxide, diazo, acyl diazo, and azoxy.

11. The method according to claim 1, wherein the 1,3 dipole is an azide.

12. A method of making an antibody-drug conjugate, comprising the step of conducting a cycloaddition reaction between:
a) an antibody comprising an N-linked oligosaccharide comprising at least one functionalized terminal sialoside; and
b) a functionalized cytotoxic drug molecule, wherein one of the functionalized terminal sialoside or functionalized cytotoxic drug molecule comprises a 1,3 dipole or 1,2,4,5 tetrazine, and the other comprises a cyclooctyne or trans cyclooctene, further comprising the step of preparing the N-linked oligosaccharide comprising at least one functionalized terminal sialoside by glycosylating an antibody comprising an N-linked oligosaccharide comprising at least one terminal galactose with a functionalized CMP-sialic acid donor in the presence of a sialyl transferase, wherein the antibody comprising an N-linked oligosaccharide comprising at least one terminal galactose is prepared by treating an antibody with a glycosyltransferase and UDP-Gal.

13. The method according to claim 12, wherein the functionalized CMP-sialic acid donor is functionalized at the C-9 or C-5 position.

14. A method of making an antibody-drug conjugate, comprising the step of conducting a cycloaddition reaction between:
a) an antibody comprising an N-linked oligosaccharide comprising at least one functionalized terminal sialoside; and
b) a functionalized cytotoxic drug molecule, wherein one of the functionalized terminal sialoside or functionalized cytotoxic drug molecule comprises a 1,3 dipole or 1,2,4,5 tetrazine, and the other comprises a cyclooctyne or trans cyclooctene, further comprising the step of preparing the N-linked oligosaccharide comprising at least one functionalized terminal sialoside by glycosylating an antibody comprising an N-linked oligosaccharide comprising at least one terminal galactose with a functionalized CMP-sialic acid donor in the presence of a sialyl transferase, wherein the functionalized CMP-sialic acid donor is selected from the group consisting of:

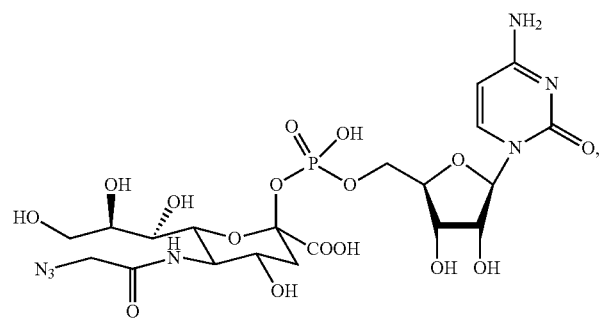

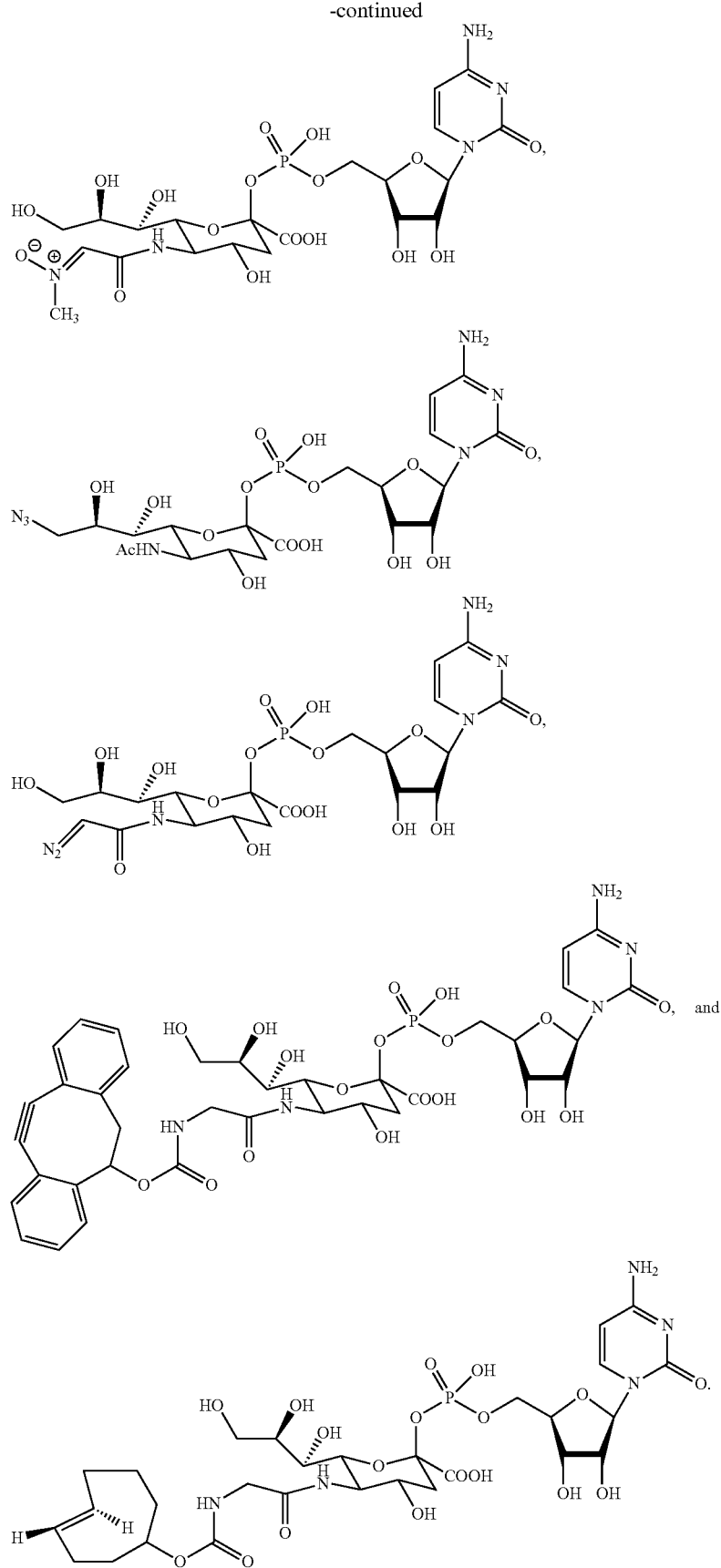

15. The method according to claim 1, wherein the N-linked oligosaccharide comprising the biantennary glycan includes a mixture of G0, G1, and G2 glycoforms.

16. The method according to claim 12, further comprising treating the antibody with a sialidase or neuraminidase prior to the treatment with glycosyltransferase and UDP-Gal.

17. The method according to claim 1, wherein the N-linked oligosaccharide comprising at least one functionalized terminal sialoside further comprises a fucose.

18. The method according to claim 1, wherein the N-linked oligosaccharide comprising at least one functionalized terminal sialoside does not include a fucose.

19. The method according to claim 1, wherein the cytotoxic drug is selected from methotrexate, taxol, mercaptopurine, thioguanine, hydroxyurea, cytarabine, cyclophosphamide, ifosfamide, nitrosourea, cisplatin, carboplatin, mitomycin, dacarbazine, procarbazine, topotecan, nitrogen mustards, cytoxan, etoposide, 5-fluorouracil, BCNU, irinotecan, camptothecin, bleomycin, doxorubicin, idarubicin, daunorubicin, dactinomycin, plicamycin, mitoxantrone, asparaginase, vinblastine, vincristine, vinorelbine, paclitaxel, calicheamicin, and docetaxel.

20. The method according to claim 1, wherein the cytotoxic drug comprises an auristatin, dolastatin, maytansinoid, pyrrolobenzodiazepine, or anthracycline.

21. The method according to claim 20, wherein the cytotoxic drug is selected from the group consisting of doxorubicin, daunorubicin, vedotin, mertansine and emtansine.

22. The method according to claim 20, wherein the cytotoxic drug comprises a pyrrolobenzodiazepine.

\* \* \* \* \*